United States Patent [19]

Draper et al.

[11] 4,172,132

[45] Oct. 23, 1979

[54] 1,3,5(10),6,8,14-19-NOR-PREGNAHEXAENES, THEIR USE AS ANTI-PSORIATIC AGENTS, AND PHARMACEUTICAL FORMULATIONS USEFUL THEREFOR

[75] Inventors: Richard W. Draper, North Caldwell; Charles J. Casmer, Rahway, both of N.J.

[73] Assignee: Schering Corporation, Kenilworth, N.J.

[21] Appl. No.: 925,724

[22] Filed: Jul. 18, 1978

Related U.S. Application Data

[63] Continuation-in-part of Ser. No. 819,182, Jul. 26, 1977, abandoned.

[51] Int. Cl.$^2$ ............................................... C07J 7/00
[52] U.S. Cl. ................................. 424/243; 260/397.45

[58] Field of Search ........................................... 424/238

[56] References Cited

U.S. PATENT DOCUMENTS

| 3,182,057 | 5/1965 | Heller et al. | 260/397.45 |
| 3,182,075 | 5/1965 | Heller et al. | 260/397.45 |

*Primary Examiner*—Elbert L. Roberts
*Attorney, Agent, or Firm*—Mary S. King

[57] ABSTRACT

1,3,5(10),6,8,14-19 Nor-pregnahexaene-20-ones exhibit anti-mitotic activity with minimal or no hormonal activity. They are particularly useful in the treatment and control of psoriasis when applied topically, a preferred anti-psoriatic compound being 16α-methyl-1,3,5(10),6,8,14-19-nor-pregnahexaene-3,17α,21-triol-20-one 21-acetate.

23 Claims, No Drawings

1,3,5(10),6,8,14-19-NOR-PREGNAHEXAENES, THEIR USE AS ANTI-PSORIATIC AGENTS, AND PHARMACEUTICAL FORMULATIONS USEFUL THEREFOR

CROSS-REFERENCE TO RELATED APPLICATION

This application is a continuation-in-part of our copending application Ser. No. 819,182 filed July 26, 1977, now abandoned.

FIELD OF INVENTION

This invention relates to novel compositions-of-matter, their use as anti-mitotic agents, and pharmaceutical formulations useful therefor.

More specifically, this invention relates to 1,3,5(10),6,8,14-19-nor-pregnahexaene-20-ones, their use in the treatment and control of psoriasis, and pharmaceutical formulations useful therefor.

PRIOR ART

Described in the art is 1,3,5(10),6,8,14-19-nor-pregnahexaene-3,17α,21-triol-20-one 3,21-diacetate and 16α,17α-isopropylidenedioxy-21-chloro-1,3,5(10),6,8,14-19-nor-pregnahexaene-3-ol-20-one 3-acetate and methods for their preparation (Heller et al, J. Am. Chem. Soc., 89, 1919 (1967)).

By this invention, we have discovered that 1,3,5(10),6,8,14-19-nor-pregnahexaene-3,ƒα,21-triol-20-one 3,21-diacetate exhibits anti-mitotic activity. Also we have made novel 1,3,5(10),6,8,14-19-nor-pregnahexaene-3,17α,21-triol-20-one derivatives and have discovered that some of them, particularly 16-substituted derivatives (preferably 16-methyl derivatives) posssess anti-mitotic activity with minimal or no hormonal side effects and, thus, are useful in the treatment of diseases characterized by rapid cell proliferation and/or abnormal cell proliferation. The 19-nor-pregnahexaene-20-ones of this invention are particularly useful in the treatment and control of psoriasis when administered topically, 16α-methyl-1,3,5(10),6,8,14-19-nor-pregnahexaene-3,17α,21-triol-20-one 21-acetate being a valuable anti-psoriatic agent having superior anti-mitotic activity at topical doses as low as 20 micrograms when tested in the mouse.

COMPOSITION-OF-MATTER ASPECT OF THE INVENTION

This invention relates to new pharmaceutical formulations comprising as active ingredient a 1,3,5(10),6,8,14-19-nor-pregnahexaene-3,17α,21-triol-20-one or derivative thereof and to the use of such formulations for the treatment and control of diseases characterized by rapid cell proliferation and/or abnormal cell proliferation. Specifically, the pharmaceutical formulations of this invention are particularly useful in the treatment and control of proliferative skin diseases, and are primarily used for the treatment of psoriasis.

Included among the active compounds of the new therapeutic formulations of this invention are 19-nor-pregnahexaene-20-ones defined by formula I:

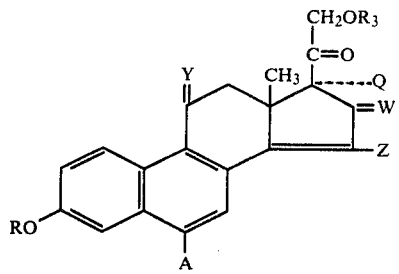

wherein
A is hydrogen, lower alkyl, fluoro, fluoromethyl, difluoromethyl, or trifluoromethyl;
R is hydrogen, lower alkyl, or an acyl radical of a hydrocarboncarboxylic acid having up to 20 carbon atoms;
Y is (H,H), (H,OH), or oxygen;
W is (H,H); (H, lower alkyl); (H-α hydroxy); H-α $OR_1$), wherein $R_1$ is an acyl radical of a hydrocarboncarboxylic acid having up to 20 carbon atoms; or =CHT wherein T is hydrogen, lower alkyl, fluorine, or chlorine;
Q is $OR_2$ wherein $R_2$ is hydrogen or an acyl radical of a hydrocarboncarboxylic acid having up to 20 carbon atoms; hydrogen provided W is (H,H), or (H, lower alkyl); or Q and W together is a 16α,17α-lower alkylidenedioxy;
Z is hydrogen, chlorine or bromine;
$R_3$ is hydrogen or an acyl radical of a hydrocarboncarboxylic acid having up to 20 carbon atoms; or $OR_3$ together with Q is a member selected from the group consisting of alkylidenedioxy and alkylorthoalkanoate;
and when Q is hydroxy and $R_3$ is hydrogen, the 17α,20;20,21-bismethylenedioxy derivatives thereof;
together with a non-toxic pharmaceutically acceptable carrier.

Lower alkyl groups included within the definition of A, R and W are preferably those having up to four carbon atoms such as methyl, ethyl, n-propyl, iso-propyl, n-butyl, sec.-butyl, and tert.-butyl, although higher homologs such as pentyl and hexyl fall within the scope of this invention.

As used in the specification and claims of this application, the term "acyl" denotes a radical derived from an acid by removal of a hydroxyl group, e.g. acetyl is the acyl radical of acetic acid; benzoyl is the acyl radical of benzoic acid.

The acyl radicals of the compounds of this invention as defined by R, $R_1$, $R_2$ and $R_3$ in formula I hereinabove include those derived from hydrocarboncarboxylic acids having up to twenty carbon atoms which may be saturated, unsaturated, straight chain or branched chain, aliphatic, cyclic, cyclic-aliphatic, aromatic, aryl-aliphatic, or alkyl-aromatic, and may be substituted by hydroxy, alkoxy containing from 1 to 5 carbon atoms, aryloxy having from 6 to 10 carbon atoms, or by a halogen. Typical ester groups of the 19-nor-pregnahexaenes of the formulations of our invention are thus derived from hydrocarboncarboxylic acids such as alkanoic acids exemplified by acetic, propionic, trimethylacetic, butyric, isobutyric, valeric, isovaleric, caproic, tert.-butylacetic, enanthic, caprylic, capric, cyclopentylpropionic, undecylic, lauric, and adamantanecarboxylic acids; substituted alkanoic acids such as phenoxyacetic, trifluoroacetic, β-chloropropionic and β-benzoylaminoisobutyric acids; aromatic and substituted aromatic acids including benzoic, toluic, p-chlorobenzoic, p-fluorobenzoic, p-methoxybenzoic, and 3',5'-dimethylbenzoic acids; aryl-alkanoic acids such as phenylacetic and phenylpropionic; unsaturated acids such as retinoic, farnesyl acetic, acrylic, sorbic and oleic acids; and dibasic acids such as succinic, tartaric, phthalic and benzene disulfonic acids.

Preferred acyl radicals as defined by R, $R_1$, $R_2$ and $R_3$ in formula I are those derived from lower alkanoic acids having preferably up to 8 carbon atoms such as radicals obtained from acetic, propionic, butyric, valeric, caprylic, caproic, tert.-butylacetic acid and the like as well as those derived from aromatic carboxylic acids having up to 8 carbon atoms, preferably from benzoic acid.

The alkylidene groups contemplated in the compounds of our invention are preferably lower alkylidenes, i.e. hydrocarbon radicals having preferably up to 4 carbon atoms including radicals such as methylene, ethylidene, n-propylidene, isopropylidene, n-butylidene, and sec.-butylidene and the like. The 16-lower alkylidene derivatives of this invention (i.e. when W in above formula I is =CHT) are double bonded to the D ring at C-16. The 16α,17α-alkylidenedioxy derivatives have the alkylidene terminal bonds attached to different oxygen atoms, i.e. to the oxygens at C-16 and C-17 in the case of the 16α,17α-alkylidenedioxy derivatives, and to oxygens at C-17 and C-21 in the case of the 17α,21-alkylidenedioxy derivatives.

The physical embodiments of the 19-nor-pregnahexaene-20-ones of the formulations of this invention are characterized by being crystalline solids, usually white to off-white in color which are insoluble in water and soluble in most organic solvents, particularly in acetone, dioxane, dimethylformamide, and dimethylsulfoxide, although of limited solubility in non-polar solvents such as dialkylethers and alkylhydrocarbons.

The 19-nor-pregnahexaene-20-ones of formula I exhibit anti-mitotic activity and, in particular, are useful in the treatment and control of psoriasis. With the exception of 1,3,5(10),6,8,14-19-nor-pregnahexaene-3,17α,21-triol-20-one 3,21-diacetate, the compounds of formula I are novel compounds. Thus, the composition-of-matter aspect of this invention resides in the concept of compounds defined by formula I exluding those wherein W, Y and Z are all hydrogen.

Useful 19-nor-pregnahexaene-20-ones of formula I include 16α-methyl-1,3,5(10),6,8,14-19-nor-pregnahexaene-3,17α,21-triol-20-one 21-acetate and the 6-methyl-, 6-fluoro-, 6-difluoromethyl- and 6-trifluoromethyl- derivatives thereof as well as the 16-desmethyl analogs and the 16β-methyl epimers thereof, 16α-hydroxy derivatives of formula I and ester and 16α,17α-alkylidenedioxy derivatives thereof such as 1,3,5(10),6,8,14-19-nor-pregnahexaene-3,16α,17α,21-tetrol-20-one 16,21-diacetate and 16α,17α-isopropylidenedioxy-1,3,5(10),6,8-19-nor-pregnahexaene-3,21-diol-20-one 21-acetate, and 16-alkylidene derivatives of formula I such as 16-methylene-1,3,5(10),6,8,14-19-nor-pregnahexaene-3,17α,21-triol-20-one 21-acetate and the 3-acetate and 3-methyl ether derivatives thereof;

16-chloromethylene-1,3,5(10),6,8,14-19-nor-pregnahexaene-3,17α,21-triol-20-one 21-acetate;

11-oxo derivatives of formula I such as 16α-methyl-1,3,5(10),6,8,14-19-nor-pregnahexaene-3,17α,21-triol-11,20-dione and the 21-acetate, 3,21-diacetate, the 3,21-dipropionate, the 3-benzoate 21-acetate, and the 3,17α,21-tripropionate esters thereof and the 16β-methyl epimers of the foregoing; and 11-hydroxy derivatives of formula I such as 16α-methyl-1,3,5(10),6,8,14-19-nor-pregnahexaene-3,11β,17α,21-tetrol-20-one and the 21-acetate, the 3,21-dipropionate and 3,17α,21-tripropionate thereof as well as their 16β-methyl epimers and the 11α-hydroxy epimers of the foregoing, and the corresponding 15-chloro- derivatives of all the foregoing.

Of the compounds of formula I, those particularly useful for the treatment of psoriasis are those having a 16-alkyl group (i.e., compounds wherein W is (H, alkyl)), particularly the 11-unsubstituted derivatives thereof, preferred compounds being 16α-methyl-1,3,5(10),6,8,14-19-nor-pregnahexaene-20-ones of formula II:

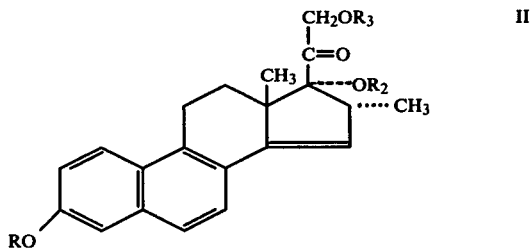

wherein R is hydrogen, lower alkyl, or an acyl radical of a hydrocarboncarboxylic acid having up to 8 carbon atoms;

$R_2$ and $R_3$ are each hydrogen or an acyl radical of a hydrocarboncarboxylic acid having up to 8 carbon atoms.

Preferred compounds of formula II thus include

16α-methyl-1,3,5(10),6,8,14-19-nor-pregnahexaene-3,17α,21-triol-20-one 21-acetate, the 3-acetate and 3-benzoate ester and the 3-methyl ether derivatives thereof; and 16α-methyl-1,3,5(10),6,8,14-19-nor-pregnahexaene-3,17α,21-triol-20-one and the 21-propionate, the 17-propionate and 17,21-di-n-butyrate ester derivatives thereof.

Of the compounds defined by formula II, particularly useful anti-psoriatic agents are the 16α-methyl derivatives wherein $R_2$ is hydrogen and, of these, especially those wherein $R_3$ is hydrogen or acetyl. Of the foregoing, a preferred species is 16α-methyl-1,3,5(10),6,8,14-19-nor-pregnahexaene-3,17α,21-triol-20-one 21-acetate, which exhibits superior anti-mitotic activity at topical doses as low as 20 micrograms when administered topically to mice in which epidermal mitosis has been stimulated by prior application of croton oil.

The 19-nor-pregnahexaene-20-ones of formula I are conveniently prepared from the corresponding 1,3,5(10),6,8-19-nor-pregnapentaene-20-ones, in which any 21-hydroxyl group present is protected, by reaction with a molar equivalent of 2,3-dichloro-5,6-dicyanobenzoquinone (DDQ) in an aprotic solvent (usually dioxane) in an essentially neutral medium. Alternatively, an 11-unsubstituted-1,4,6,8,14-pregnapentaene-3,20-dione can be subjected to aromatization, e.g., by means of a weak base in the presence of a soluble halide salt such as lithium chloride to obtain the corresponding 11-unsubstituted-1,3,5(10),6,8,14-19-nor-pregnahexaene-3-ol-20-one. Also, a 9α,11β-dihalogeno-1,4,6-pregnatriene-3,20-dione can be subjected to concomitant didehydrohalogenation and aromatization or a 9α,11β-dichloro-1,4-pregnadiene-3,20-dione can be subjected to concomitant 6-dehydrogenation, didehydrochlorination and aromatization in situ at elevated temperatures by means of DDQ as dehydrogenating agent and in the presence of acid in an aprotic solvent to obtain the corresponding 11-unsubstituted 1,3,5(10),6,8,14-19-nor-pregnahexaene-3-ol-20-one. Isolation of the respective 19-nor-pregnahexaene-3-ol-20-ones of this invention is then effected by methods well known in the steroid art. When the 14-dehydrogenation of a 1,3,5(10),6,8-19-nor-pregnapentaene is carried out in the presence of at least a molar equivalent of hydrogen chloride and with about two molar equivalents of DDQ, there are formed the 15-chloro-19-nor-pregnahexaene-20-ones of formula I, also novel compounds of this invention. Thus, for example, reaction of 16α-methyl-1,3,5(10),6,8-19-nor-pregnapentaene-3,17α,21-triol-20-one 21-acetate in dioxane with at least a molar equivalent of hydrogen chloride and with about two molar equivalents of DDQ yields 15-chloro-16α-methyl-1,3,5(10),6,8,14-19-nor-pregnahexaene-3,17α,21-triol-20-one 21-acetate, having antimitotic activity. Similarly, by substituting hydrogen bromide for hydrogen chloride, there is obtained the corresponding 15-bromo compounds of formula I.

The foregoing process for preparing the 15-chloro derivatives of this invention is preferably carried out at room temperature (although temperatures in the range of from about 0° to 100° C. may be employed) and in dioxane (although other aprotic solvents may be used, particularly ethers such as tetrahydrofuran, diethylether and diglyme). When carried out at room temperature, the reaction is usually complete in 30 minutes as determined by thin layer chromatography, although at lower temperatures it may take up to 24 hours before complete conversion of a 1,3,5(10),6,8-19-nor-pregnapentaene-20-one to the corresponding 15-chloro-14-dehydro compound has been effected. Although, in our process, only a molar equivalent of hydrogen chloride is required per mole of pregnapentaene-20-one starting compound, we prefer to use large excesses of hydrogen chloride (e.g. a saturated solution of hydrogen chloride in dioxane) since the rate of reaction is thereby increased and the process is completed in thirty minutes or less.

Many of the 1,3,5(10),6,8-19-nor-pregnapentaene-20-one precursors of the 11-unsubstituted-19-nor-pregnahexaene-20-ones of this invention are known in the art (e.g., being described in U.S. Pat. Nos. 3,182,057 and 3,182,075) and are prepared by reaction of a 9α,11β-dichloro-1,4-pregnadiene-17α,21-diol-3,20-dione 21-alkanoate (e.g., 16α-methyl-9α,11β-dichloro-1,4-pregnadiene-17α,21-diol-3,20-dione 21-acetate) with a weak base, preferably in the presence of lithium chloride. Weak bases useful in this process may be pyridine, collidine, lutidine and, preferably, dimethylformamide. Other 11-unsubstituted-19-nor-pregnapentaene-20-one precursors may also be prepared from the corresponding 9α,11β-dichloro-1,4-pregnadiene-3,20-diones in similar manner.

The 9α,11β-dichloro-1,4-pregnadiene-17α,21-diol-3,20-dione precursors to the 11-unsubstituted-1,3,5(10),6,8-19-nor-pregnapentaene-20-one intermediates are also known in the art, being prepared from the corresponding 9(11)-dehydro derivatives according to procedures such as described in U.S. Pat. Nos. 2,894,963 and 3,009,933.

Alternatively, the 11-unsubstituted-3-hydroxy-1,3,5(10),6,8-19-nor-pregnapentaene-20-one intermediates are conveniently prepared from the corresponding 1,4,6,9(11)-pregnatetraene-3,20-diones by reaction with a nucleophilic acid (e.g., hydrochloric or hydrobromic acid) in an aprotic solvent (e.g., dioxane) whereby is formed a mixture of a 3-hydroxy-1,3,5(10),6,8-19-nor-pregnapentaene-20-one and the 3-methyl ether thereof which is isolated and separated via chromatographic techniques.

When preparing the 11-oxygenated derivatives of formula I, it is preferable to introduce the 11-oxygen function prior to aromatization of the A and B rings. Of the requisite 11-oxygenated 19-nor-pregnapentaene precursors, described in the art is 11β-hydroxy-1,3,5(10),6,8-19-nor-pregnapentaene-3,17α,21-triol-21-acetate and its preparation from 9α-bromo-1,4,6-pregnatriene-11β,17α,21-triol-3,20-dione 21-acetate by reaction with pyridine at reflux temperature. Similar treatment with pyridine of other 9α-bromo-11β-hydroxy-1,4,6-pregnatriene derivatives, e.g., 9α-bromo-16α-methyl-1,4,6-pregnatriene-11β,17α,21-triol-3,20-dione 21-acetate will produce other 11β-hydroxy-19-nor-pregnapentaene precursors, e.g., 16α-methyl-1,3,5(10),6,8-19-nor-pregnapentaene-3,11β,17α-tetrol-20-one 21-acetate.

11-Oxo-19-nor-pregnapentaene starting compounds can be prepared from a 9α-bromo-11-oxo-1,4-pregnadiene when subjected to enol benzoylating conditions. Thus, for example, 9α-bromo-16α-methyl-1,4-pregnadiene-17α,21-diol-3,11-20-trione 21-acetate, upon reaction with benzoyl chloride in pyridine yields 16α-methyl-1,3,5(10),6,8-19-nor-pregnapentaene-3,17α,21-triol-11,20-dione 3-benzoate 21-acetate.

Alternatively, both 11-oxo- and 11β-hydroxy-19-nor-pregnapentaene starting compounds may be prepared from the corresponding 3-oxo-1,4,6,8-pregnatetraene by treatment thereof under aromatizing conditions such as by reaction in tetrahydrofuran in the presence of acid or by reaction with lithium chloride in dimethylformamide in the presence of acid. Thus, for example, treatment of 16β-methyl-1,4,6,8-pregnatetraene-11β,17α,21-triol-3,20-dione 21-acetate in tetrahydrofuran with hydrochloric acid yields an 11β-hydroxy-19-nor-pregnapentaene precursor of the compounds of this invention, e.g., 16β-methyl-1,3,5(10),6,8-19-nor-pregnapentaene-3,11β,17α,21-tetrol-20-one 21-acetate. The requisite 3-oxo-11-oxygenated 1,4,6,8-pregnatetraenes are, in turn, derived from the corresponding 3-oxo-9α-halogeno-1,4,6-pregnatriene by treatment with base. For example, 9α-chloro-16β-methyl-1,4,6-pregnatriene-11β,17α,21-triol-3,20-dione 21-acetate, upon reaction with potassium acetate in methanol, yields 16β-methyl-1,4,6,8-pregnatetraene-11β,17α,21-triol-3,20-dione 21-acetate. If desired, when carrying out the foregoing dehydrohalogenation at C-8(9) with introduction of a double bond at C-8, one can simultaneously oxidize an 11β-hydroxy group to an 11-oxo function according to known procedures. Thus, treatment of 9α-bromo-11β-hydroxy-1,4,6-pregnatriene-17α,21-diol-3,20-dione 21-acetate in pyridine with chromic acid yields 11-oxo-1,4,6,8-pregnatetraene-17α,21-diol-3,20-dione 21-acetate. Alternatively, a 1,4,6,8-pregnatetraene-11β,17α,21-triol-3,20-dione may be oxidized to the corresponding 11-oxo derivative with manganese dioxide prior to aromatization and introduction of the double bond at C-14.

When preparing 11-hydroxy-1,3,5(10),6,8,14-19-nor-pregnahexaenes of formula I, one can treat the corresponding 11-hydroxy-1,3,5(10),6,8-19-nor-pregnapentaene with DDQ as described hereinabove. Alternately, one may reduce the corresponding 11-oxo-19-nor-pregnahexaene of formula I by means of agents known to reduce oxo functions to hydroxyl, such as with sodium borohydride. When carrying out this reaction, it is necessary to block the 20-oxo function in the dihydroxy acetone side chain at C-17 so that the 20-oxo function will not be reduced. Protection of the 20-oxo function may be effected via known methods such as by preparing a 17α,20;20,21-bismethylenedioxy derivative or by preparing a 17,21-diester. When reducing an 11-oxo-19-nor-pregnahexaene of formula I to the corresponding 11-hydroxy-19-nor-pregnahexaene, there is usually obtained a mixture of the 11α-hydroxy and 11β-hydroxy epimers which are separable by chromatographic techniques. Thus, for example, treatment of 16α-methyl-1,3,5(10),6,8,14-19-nor-pregnahexaene-3,17α,21-triol-11,20-dione 3,17,21-tripropionate with sodium borohydride yields a mixture of the corresponding 11α- and 11β-hydroxy derivatives together with the corresponding 3,11β-dihydroxy derivatives which, after separation via chromatography over silica gel and hydrolysis of the ester functions by means of methanolic sodium bicarbonate, yields 16α-methyl-1,3,5(10), 6,8,14-19-nor-pregnahexaene-3,11β,17α,21-tetrol-20-one and the corresponding 11α-hydroxy derivative of formula I, respectively.

When preparing a 16-alkylidene compound of formula I (i.e. a compound wherein W is =CHT), one may start with a 9α,11β-dichloro-16-alkylidene-1,4-pregnadiene-17α,21-diol-3,20-dione 21-lower alkanoate precursor and convert it to a 16-alkylidene-1,3,5(10),6,8-19-nor-pregnapentaene and thence to the 14-dehydro analog of formula I according to the process described hereinabove.

Alternatively, to minimize side reactions which occur when halogenating a 9(11)-dehydro-16-alkylidene-17α-hydroxy-1,4-pregnadiene-3,20-dione, one may protect the 17α-hydroxyl function thereof such as by esterification after introduction of the 9(11) double bond. After preparing the corresponding 9α,11β-dichloro derivative of the 17α-hydroxy protected derivative of a 16-alkylidene-1,4,9(11)-pregnatriene-3,20-dione (e.g. 16-methylene-9α,11β-dichloro-1,4-pregnadiene-17α,21-diol-3,20-dione 17,21-diacetate) and thence conversion thereof to a 16-alkylidene-1,3,5(10),6,8,14-19-nor-pregnahexaene-3-ol of formula I (e.g. 16-methylene-1,3,5(10),6,8,14-19-nor-pregnahexaene-3,17α,21-triol-20-one 17,21-diacetate), the 17α-hydroxy protecting groups may be easily removed via known techniques (e.g. by means of aqueous sodium bicarbonate in methanol) to obtain a 16-alkylidene-1,3,5(10),6,8,14-19-nor-pregnahexaene-3,17α,21-triol-20-one of this invention (e.g. 16-methylene-1,3,5(10),6,8,14-19-nor-pregnahexaene-3,17α,21-triol-20-one).

When converting a 1,3,5(10),6,8-19-nor-pregnapentaene-20-one to the corresponding 1,3,5(10),6,8,14-19-nor-pregnahexaene-20-one by reaction with DDQ as described hereinabove, it is preferable that any 21-hydroxyl group which may be present be protected, such as by an acyl function. We prefer to utilize lower alkanoate ester derivatives (usually acetates) of the 19-nor-pregnapentaene-20-one precursors, therefore, the 19-nor-pregnahexaene-20-ones of formulae I and II are produced as 21-alkanoates, usually 21-acetates. The corresponding 21-hydroxy compound is then easily derived from the 21-alkanoate via known hydrolytic procedures, such as with aqueous sodium bicarbonate in methanol or by utilizing diastase enzyme of malt in aqueous ethanol using known procedures.

In general, when a 21-mono-lower alkanoate or a 17,21-dilower alkanoate derivative of a 3-hydroxy-19-nor-pregnahexaene-20-one of formula I is desired, it is preferable to use as starting compound a 19-nor-1,3,5(10),6,8-pregnapentaene-20-one precursor containing the desired 21-mono-alkanoate or 17,21-dialkanoate ester function prior to reaction with DDQ.

A 17-mono-lower alkanoate ester derivative of a 3-hydroxy-19-nor-pregnahexaene-20-one of formula I may be prepared by reaction of an unesterified precursor (e.g. 16α-methyl-1,3,5(10),6,8,14-19-nor-pregnahexaene-3,17α,21-triol-20-one) in an aprotic solvent (e.g. dimethylsulfoxide) with at least one molar equivalent of a trilower alkyl ortho ester (e.g. triethylorthopropionate) in the presence of a strong acid (e.g. p-toluene-sulfonic acid) followed by hydrolytic cleavage of the resulting 17α,21-ortho ester by means of aqueous acid (e.g. aqueous acetic acid), thence separation and isolation of the 17-mono-ester using known techniques, usually including chromatographic methods, whereby is obtained a 17-mono-alkanoate (e.g. the 17-propionate). By this procedure, there is usually also produced some of the corresponding 21-mono-alkanoate derivatives (e.g. the 21-propionate) which may also be isolated via chromatographic techniques.

A 3,17α-diester derivative of formula I is conveniently derived from a 3-hydroxy-17α,21-orthoester intermediate (prepared as described hereinabove) by reaction thereof with an acid anhydride or acid halide in pyridine (e.g. acetic anhydride in pyridine) to form the corresponding 3-alkanoate 17α,21-orthoester intermediate which, after hydrolytic cleavage of the 17α,21-orthoester group by means of aqueous acetic acid, yields a 3,17-diester of formula I.

The 3,21-diester derivatives are conveniently prepared from the corresponding 21-monoester, the 3,17α,21-triesters may be prepared from the corresponding 17α,21- or 3,17α-diesters utilizing conventional esterification techniques. When esterifying a 3-hydroxyl group in the presence of an 11-hydroxyl group, the reaction is preferably carried out utilizing only one equivalent of acylating agent to minimize the formation of a 3,11-diester. Similarly, when converting a 3,11,21-trihydroxy compound of formula I to the corresponding 3,21-diester, only two equivalents of acylating agent are employed.

To prepare a 3-monoester derivative of formula I it is necessary to protect the 21-hydroxyl group (e.g., by an ether derivative such as the 21-methoxyethoxymethyl ether) in the 9α,11β-dichloro-1,4-pregnadiene-20-one precursor (e.g., by reaction of 16α-methyl-9α,11β-dichloro-1,4-pregnadiene-17α,21-diol-3,20-dione with triethylmethoxyethoxymethylammonium chloride in acetonitrile) prior to reaction thereof with a weak base in the presence of lithium chloride to produce the corresponding 3-hydroxy-1,3,5(10),6,8-19-nor-pregnapentaene-20-one (e.g., 16α-methyl-1,3,5(10),6,8,19-nor-pregnapentaene-3,17α,21-triol-20-one 21-methoxyethoxymethyl ether). Reaction of the 21-protected-1,3,5(10),6,8-19-nor-pregnapentaene-20-one with DDQ yields the corresponding 1,3,5(10),6,8,14-19-nor-pregnahexaene-20-one (e.g. 16α-methyl-1,3,5(10),6,8,14-19-nor-pregnahexaene-3,17α,21-triol-20-one 21-methoxyethoxymethyl ether) which, upon treatment thereof according to standard esterification procedures (e.g. by reaction with acetic anhydride in pyridine), yields the corresponding 3-monoester 21-methoxyethoxymethyl ether derivative. Upon cleavage of the 21-ether function, e.g. by means of zinc bromide in methylene chloride, there is then produced a 3-monoester of formula I (e.g. 16α-methyl-1,3,5(10),6,8,14-19-nor-pregnahexaene-3,17α,21-triol-20-one 3-acetate).

The 3-alkoxy derivatives of formula I are prepared via known etherification techniques such as those utilizing a diazoalkane (e.g. diazomethane in ether). Thus, a 3-alkoxy 21-ester or a 3-alkoxy 17,21-diester derivative is prepared from the corresponding 3-hydroxy 21-ester or 3-hydroxy 17,21-diester derivatives by reaction with a diazoalkane in ether.

A derivative of formula I having a 3-alkoxy group and hydroxyl functions at 17 and 21 may be conveniently derived from a 3-alkoxy 21-ester derivative via hydrolysis such as with aqueous sodium bicarbonate in methanol.

In order to prepare a 3-alkoxy 17-ester derivative of a compound of formula I (e.g. 16α-methyl-1,3,5(10),6,8,14-19-nor-pregnahexaene-3,17α,21-triol-20-one 17-acetate 3-methyl ether) it is preferable to first prepare a 17α,21-orthoester derivative of a 3,17α,21-triol of formula I according to procedures described hereinabove followed by reaction thereof with a diazoalkane (e.g. diazomethane) to produce a 3-alkoxy-17α,21-orthoester derivative followed by cleavage of the 17α,21-orthoester by means of dilute acid to obtain a 3-alkoxy 17-ester derivative of formula I.

When preparing a 16α,17α-alkylidenedioxy derivative of formula I, the 16α,17α-alkylidenedioxy function may be introduced into the molecule prior to or after preparation of the corresponding 16α,17α-dihydroxy-1,3,5(10),6,8,14-19-nor-pregnahexaene-20-one; however, a 17α,21-alkylidenedioxy derivative of formula I is usually introduced after preparation of the corresponding 17α,21-dihydroxy-1,3,5(10),6,8,14-19-nor-pregnahexaene-20-one. Both the 16α,17α- or 17α,21-alkylidenedioxy derivatives of the 1,3,5(10),6,8,14-19-nor-pregnahexaene-20-ones of formula I are prepared from the corresponding 16α,17α-dihydroxy- or 17α,21-dihydroxy-steroid upon reaction with a ketone or aldehyde (e.g. acetone, acetaldehyde, acetophenone) in the presence of a mineral acid (e.g. hydrochloric acid).

The 17α,20;20,21-bismethylenedioxy function can be introduced prior to or after introduction of the 19-nor-pregnapentaene or 19-nor-pregnahexaene system by known reactions such as that utilizing formaldehyde in the presence of acid.

THE METHOD OF USE AND PHARMACEUTICAL FORMULATION ASPECTS OF THE INVENTION

The method-of-use aspect of this invention resides in the concept of the method of eliciting a mitotic inhibitory response in a warm-blooded animal having a disease characterized by rapid cell proliferation which comprises administering to said animal a non-toxic, mitotic-inhibitory effective amount of a 19-nor-pregnahexaene-20-one of formula I defined hereinabove, together with a non-toxic, pharmaceutically acceptable carrier.

Our method is particularly useful in the treatment and control of proliferative skin diseases, and is primarily useful for the treatment of psoriasis via the topical route.

Psoriasis is characterized by increased epidermipoiesis associated with a high mitotic rate, rapid cell turnover and altered keratinization. The psoriatic epidermis can be normalized by slowing down cell growth through inhibiting mitosis.

All drugs currently used in psoriasis therapy are known to directly or indirectly reduce epidermal mitotic activity. Although there is no animal model for psoriasis, many of these same drugs have been reported to have a similar effect in models of epidermal hyperplasia which simulate psoriasis in laboratory animals.

Topically effective anti-psoriatic drugs, including corticosteroids, anthralin, coal tar and 5-fluorouracil, while relatively free of systemic side effects, cause local adverse reactions. Thus, corticosteroid therapy causes skin atrophy, telangiectasia and the formation of striae, while anthralin and 5-fluorouracil are skin irritants and require close clinical supervision for optimal therapeutic benefit. Anthralin can also cause staining of the skin.

By our invention, we have discovered that 1,3,5(10),6,8,14-19-nor-pregnahexaene-3,17α,21-triol-20-one and derivatives thereof (particularly 16α-methyl-1,3,5(10),6,8,14-19-nor-pregnahexaene-3,17α,21-triol-20-one 21-acetate) reduce epidermal mitotic activity without causing significant local or systemic hormonal or toxic effects when applied topically to the skin of mice in which epidermal mitosis has been stimulated.

Specifically, when treated by a procedure modified from S. Belman and W. Troll, Cancer Research 32:450–454 (1972), the 19-nor-pregnahexaene-20-ones of this invention, particularly the 16α-methyl derivatives of formula II, reduce croton-oil stimulated epidermal mitosis in mice when applied topically. Moreover, the 19-nor-pregnahexaene-20-ones are non-irritating without causing hormonal side effects which is surprising in view of the structure of the 19-nor-pregnahexaene-20-ones which has an aromatic A ring such as in many estrogens, and a corticoid side chain as in potent topical anti-inflammatory agents such as dexamethasone 17-valerate and betamethasone dipropionate.

In the foregoing test, croton-oil is applied topically to shaved mice, thus accelerating mitosis. A 1,3,5(10),6,8,14-19-nor-pregnahexaene-3,17α,21-triol-20-one of this invention is applied topically to the stimulated site, then 24 hours later portions of the treated skin are excised for histologic processing, mitotic figures per thousand basal interfollicular epidermal cells being counted in a light microscope. Epidermal mitotic counts from drug-treated mice are compared to counts from lesion controls for statistically significant differences with an analysis of variance. The mitotic count for each compound tested is expressed as percent reduction of mitoses compared with the number of mitoses on the skin of mice treated with croton-oil alone. In general, it was discovered that the 19-nor-pregnahexaene-20-ones of this invention such as are defined by formula I significantly reduce croton-oil stimulated epidermal mitosis. For example, the 16α-methyl-19-nor-pregnahexaene-20-ones of formula II usually exhibit over 60% inhibition of mitoses at a 2 mg. topical dose. 16α-Methyl-1,3,5(10),6,8,14-19-nor-pregnahexaene-3,17α,21-triol-20-one 21-acetate (a preferred compound of the invention) exhibits about 80% reduction of mitosis (even at a topical dose as low as 0.2 mg.) which is approximately 10 times greater than the mitotic reduction exhibited by an equal quantity (i.e. 0.2 mg.) of betamethasone dipropionate (a known anti-psoriatic agent) in the same animal model.

The anti-mitotic activity of the 19-nor-pregnahexaene-20-ones is also demonstrated by similar tests in mice whereby increased epidermal mitosis is produced by ultraviolet irradiation according to procedures modified from A. DuVivier and R. B. Stoughton, J. Investigative Dermatology, 65:233–237 (1975). In these tests, it was demonstrated that the 19-nor-pregnahexaene-20-ones of this invention, particularly 16α-methyl-1,3,5(10),6,8,14-19-nor-pregnahexaene-3,17α,21-triol-20-one 21-acetate, significantly reduces epidermal mitotic rate following 1, 5 or 9 topical applications (at 0.02 mg., 0.10 mg., or 0.5 mg. doses) to ultraviolet stimulated hairless mouse epidermis, advantageously causing an epidermal thinning effect after multiple applications when the effect became equivalent to that domonstrated by steroidal anti-psoriatic agents such as betamethasone valerate. Since the compounds of this invention such as defined by formulae I and II do not cause estrogenic or other hormonal or toxic effects when applied topically as demonstrated by tests in mice, continued application of a 19-nor-pregnahexaene-20-one of this invention will not cause irritation or staining of the skin or skin atrophy as caused by known anti-psoriatic agents.

The foregoing mode of anti-psoriatic activity of the 19-nor-pregnahexaene-20-ones of this invention is different from that demonstrated by steroidal anti-psoriatic agents such as the well-known betamethasone valerate which, when applied topically to ultraviolet stimulated hairless mouse epidermis at doses equal to those of our 19-nor-pregnahexaene-20-ones (e.g. 16α-methyl-1,3,5(10),6,8,14-19-nor-pregnahexaene-3,17α,21-triol-20-one 21-acetate) first causes an epidermal thinning without reduction of mitoses.

A preferred compound of this invention is 16α-methyl-1,3,5(10),6,8,14-19-nor-pregnahexaene-3,17α,21-triol-20-one 21-acetate which, when applied topically to mice, significantly reduces croton-oil induced epidermal mitoses, being about 10 times as potent as betamethasone dipropionate. Our preferred compound also reduces ultraviolet induced epidermal mitoses and epidermal thickness in mice, being as active as the well known steroidal anti-psoriatic agent betamethasone 17-valerate, with a mode of action advantageously dependent on its primary activity as an anti-mitotic agent.

The 19-nor-pregnahexaene-20-ones of this invention, particularly 16α-methyl-1,3,5(10),6,8,14-19-nor-pregnahexaene-3,17α,21-triol-20-one 21-acetate, have also been found to exhibit anti-mitotic activity when administered orally or parenterally to mice without causing significant local or systemic hormonal or toxic effects.

In view of the anti-mitotic and anti-acanthotic activity in mice of the 19-nor-pregnahexaene-20-ones of this invention, particularly when applied topically, our invention includes the concept of the method of treating and controlling psoriasis which comprises applying topically to the affected area in a concentration effective for the treatment of psoriasis, a 19-nor-pregnahexaene-20-one of formula I together with a non-toxic pharmaceutically acceptable carrier. Preferred anti-psoriatic agents of this invention are the 16-methyl-19-nor-pregnahexaene-20-ones of formula II, particularly 16α-methyl-1,3,5(10),6,8,14-19-nor-pregnahexaene-3,17α,21-triol-20-one 21-acetate and the 3-acetate, 3-benzoate and 15-chloro derivatives thereof.

Included within the term "topically applying" are topical applications on skin whereby our compounds are effective in the treatment and control of skin diseases characterized by rapid cell proliferation and/or abnormal cell proliferation, e.g. psoriasis; also included are aerosol application and subcutaneous injection application which are effective in the treatment of local epidermal disorders.

When carrying out a preferred mode of our method, a pharmaceutical formulation comprising a 19-nor-pregnahexaene-20-one of formula I, preferably a 16α-methyl compound of formula II such as 16α-methyl-1,3,5(10),6,8,14-19-nor-pregnahexaene-3,17α,21-triol-20-one 21-acetate, together with a non-toxic pharmaceutically acceptable carrier, usually in concentrations in the range of from about 0.0001 percent to about 5 percent, preferably from about 0.1 percent to about one percent, is applied several times daily to skin affected by psoriasis until the psoriatic condition has improved. Topical applications of the 19-nor-pregnahexaene-20-one may then be continued at less frequent intervals (e.g. once a day) to control mitoses in order to prevent return of severe psoriatic conditions.

The 19-nor-pregnahexaene-20-ones of formula I and, preferably, II, are conveniently applied in a liquid solvent, preferably in a water-miscible liquid carrier made up of hydrophylic liquids having a high solvating action, e.g. a solution of 16α-methyl-1,3,5(10),6,8,14-19-nor-pregnahexaene-3,17α,21-triol-20-one 21-acetate together with polyethylene glycol. In general, the 19-nor-pregnahexaene-20-ones may be applied in any topical form including creams, lotions, aerosols and ointments, which are prepared by combining the ingredient, e.g. a 19-nor-pregnahexaene such as defined by formula I, with conventional pharmaceutical diluents and carriers used in topical formulations comprising steroids.

Thus, the pharmaceutical formulation aspect of this invention resides in the concept of a pharmaceutical composition for the treatment of psoriasis, preferably for topical application, comprising an anti-psoriatic effective amount of a 19-nor-pregnahexaene-20-one of formula I together with a non-toxic, pharmaceutically acceptable carrier.

Preferred are topical formulations comprising 16α-methyl-19-nor-pregnahexaene-20-ones of formula II, particularly 16α-methyl derivatives thereof having a hydroxyl function at C-17, pharmaceutical formulations comprising 16α-methyl-1,3,5(10),6,8,14-19-nor-pregnahexaene-3,17α,21-triol-20-one 21-acetate being particularly valuable.

The pharmaceutical formulations are made according to known procedures, some of which are described in detail in the Examples hereinbelow. Typical formulations include ointments, lotions, creams, sprays, powders, drops (e.g. ear drops), suppositories, and aerosols. Ointments and creams may, for example, be formulated with an aqueous or oily base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, polyethylene glycols, woolfat, hydrogenated lanolin, beeswax, etc.

Lotions may be formulated with an aqueous or oily base and will, in general, also include one or more of the following, namely, stabilizing agents, emulsifying agents, dispersing agents, suspending agents, thickening agents, coloring agents, perfumes and the like.

Powders may be formed with the aid of any suitable powder base, e.g. talc, lactose, starch, etc. Drops may be formulated with an aqueous base or non-aqueous base also comprising one or more dispersing agents, suspending agents, solubilizing agents, etc.

The topical pharmaceutical compositions according to the invention may also include one or more preservatives or bacteriostatic agents, e.g. methyl hydroxybenzoate, propyl hydroxybenzoate, chlorocresol, benzalkonium chlorides, etc.

The compositions according to the invention may also contain other active ingredients such as antimicrobial agents, particularly antibiotics.

In addition to the topical pharmaceutical compositions of the invention described in detail hereinabove and in the formulations below, our inventive concept includes pharmaceutical formulations for administration orally or parenterally, made according to standard procedures and comprising an anti-mitotic amount of a 1,3,5(10),6,8,14-19-nor-pregnahexaene-20-one of formula I together with a non-toxic, pharmaceutically acceptable carrier.

The proportion of active steroid in the topical compositions according to the invention depends on the precise type of formulations to be prepared but will generally be within the range of from 0.0001% to 5% by weight. Generally, however, for most types of topical preparations the proportion of active steroid used will be within the range of from 0.1 to 3% and preferably 0.1% to 1%.

Based upon studies in mice, when administered systemically, preferably parenterally, the dosage necessary to produce an anti-mitotic response is in the range of from about 1 to about 100 mg. per kilogram body weight.

The following formulations exemplify some of the dosage forms in which the anti-mitotic agents of our invention may be employed. In each, the active ingredient is 16α-methyl-1,3,5(10),6,8,14-19-nor-pregnahexaene-3,17α,21-triol-20-one 21-acetate. It is understood, however, that this compound may be replaced by equivalent quantities of other active 19-nor-pregnahexaenes of this invention, e.g. by the 3-acetate, the 3-benzoate or 15-chloro derivative of 16α-methyl-1,3,5(10),6,8,14-19-nor-pregnahexaene-3,17α,21-triol-20-one 21-acetate.

FORMULATIONS

Formulation I: Ointment

| Formula | mg/g |
| --- | --- |
| 16α-methyl-1,3,5(10),6,8,14-19-nor-pregnahexaene-3,17α,21-triol-20-one 21-acetate, Micronized | 1.0–20.0 |
| Benzyl Alcohol, NF | 10.0 |
| Mineral Oil, USP | 50.0 |
| White Petrolatum, USP to make | 1.0 g |

Procedure

Mix and heat to 65° C. a weighed quantity of white petrolatum, mineral oil, benzyl alcohol, and cool to 50°–55° C. with stirring. Disperse 16α-methyl-1,3,5(10),6,8,14-19-nor-pregnahexaene-3,17α,21-triol-20-one 21-acetate in a portion of the mineral oil and then add to the above mixture with stirring. Cool to room temperature.

Formulation II: Cream

| Formula | mg/g |
| --- | --- |
| 16α-methyl-1,3,5(10),6,8,14-19-nor-pregnahexaene-3,17α,21-triol-20-one 21-acetate | 1.0–20.0 |
| Stearic Acid, USP | 60.0 |
| Glyceryl Monostearate, Cosmetic | 100.0 |
| Propylene Glycol, USP | 50.0 |
| Polyethylene Sorbitan Monopalmitate | 50.0 |
| Sorbitol Solution, USP | 30.0 |
| Benzyl Alcohol, NF | 10.0 |
| Purified Water, USP to make | 1.0 g |

Procedure

Heat the stearic acid, glyceryl monostearate and polyethylene sorbitan monopalmitate to 70° C. In a separate vessel, dissolve sorbitol solution, benzyl alcohol, water, and half quantity of propylene glycol and heat to 70° C. Add the aqueous phase to oil phase with high speed lightning stirring. Dissolve the 16α-methyl-1,3,5(10),6,8,14-19-nor-pregnahexaene-3,17α,21-triol-20-one 21-acetate in remaining quantity of propylene glycol and add to the above emulsion when the temperature of emulsion is 37°–40° C. Mix uniformly with stirring and cool to room temperature.

Formulation III: Gel

| Formula | mg/g |
| --- | --- |
| 16α-methyl-1,3,5(10),6,8,14-19-nor-pregnahexaene-3,17α,21-triol-20-one 21-acetate | 1.0–20.0 |
| Propylene Glycol, USP | 300.0 |
| Butylated Hydroxytoluene | 5.0 |
| Carbomer 940 | 5.0 |
| Sodium Hydroxide (added as a 1% w/w solution in propylene glycol) | 0.7 |
| Polyethylene Glycol 400, USP | 669.3–688.3 |

Procedure

Prepare a 1% solution of the sodium hydroxide in propylene glycol and hold. Add approximately one-half the remaining propylene glycol, and the polyethylene glycol 400 to a suitable vessel and mix. Dissolve the butylated hydroxytoluene in this mixture. Disperse the carbomer 940 in the above mixture with vigorous agitation. Add the solution of sodium hydroxide with high speed agitation to bring pH up to 7 and recirculation until a thick gel forms. Dissolve the 16α-methyl-1,3,5(10),6,8,14-19-nor-pregnahexaene-3,17α,21-triol-20-one 21-acetate in the remaining propylene glycol and add to the gel slowly as the gel is continuously recirculated.

Formulation IV: Lotion

| Formula | mg/g |
| --- | --- |
| 16α-methyl-1,3,5(10),6,8,14-19-nor-pregnahexaene-3,17α,21-triol-20-one 21-acetate | 1.0–20.0 |
| Carbomer 940 (G.W. Goodrich) | 3.0 |
| Sodium hydroxide (charged as 4% w/w aqueous solution) | 0.05 |
| Isopropyl Alcohol | 40.00 |
| Purified Water, USP to make | 1.0 g |

Procedure

Prepare a 4% solution of sodium hydroxide in water. Heat the purified water to 60° C. Add carbomer 940 and mix at high speed until dispersed. Cool the above mixture to room temperature and slowly change sodium hydroxide solution until uniform. Add 80% of isopropyl alcohol to the above with mixing. Dissolve 16α-methyl-1,3,5(10),6,8,14-19-nor-pregnahexaene-3,17α,21-triol-20-one 21-acetate in remaining isopropanol. Add this to the mixture with stirring. Adjust pH to 5.0 to 5.5 with sodium hydroxide, if necessary.

| Formula | Formulation V: Tablet | | |
|---|---|---|---|
| | 10 mg. Tab. | 25 mg. Tab. | 100 mg. Tab. |
| 16α-methyl-1,3,5(10),6,8,14-19-nor-pregnahexaene-3,17α,21-triol-20-one 21-acetate | 10.5* mg. | 26.25* mg. | 105.0* mg. |
| Lactose, impalpable powder | 197.50 mg. | 171.25 mg. | 126.00 mg. |
| Corn Starch | 25.00 mg. | 25.00 mg. | 35.00 mg. |
| Polyvinylpyrrolidone | 7.50 mg. | 7.50 mg. | 7.50 mg. |
| Magnesium Stearate | 2.50 mg. | 2.50 mg. | 3.50 mg. |

*5% excess

Procedure

Prepare a slurry consisting of 16α-methyl-1,3,5(10),6,8,14-19-nor-pregnahexaene-3,17α,21-triol-20-one 21-acetate, lactose and polyvinylpyrrolidone. Spray dry the slurry. Add the corn starch and magnesium stearate. Mix and compress into tablets.

| Formulation VI: Parenteral Compositions | |
|---|---|
| Intramuscular or Subcutaneous Oil Injection | |
| Formula | mg/ml |
| 16α-methyl-1,3,5(10),6,8,14-19-nor-pregnahexaene-3,17α,21-triol-20-one 21-acetate | 1–20 |
| Aluminum Monostearate, USP | 20.0 |
| Propylparaben, USP | 1.0 |
| Sesame Oil, USP (heat treated) q.s. ad | 1.0 ml. |
| B. Intramuscular or Subcutaneous Aqueous Suspension | |
| Formula | mg/ml |
| 16α-methyl-1,3,5(10),6,8,14-19-nor-pregnahexaene-3,17α,21-triol-20-one 21-acetate | 1–20 |
| Monobasic sodium phosphate | 6.0 |
| Dibasic sodium phosphate Anhydrous | 0.5 |
| Polysorbate 80, USP | 0.05 |
| Benzyl Alcohol, R | 9.0 |
| Methylparaben, USP | 1.3 |
| Propylparaben, USP | 0.2 |
| Sodium Chloride, USP | 2.5 |
| Sodium Carboxymethylcellulose, USP | 3.0 |
| Disodium Edetate, USP | 0.1 |
| Water for Injection, USP q.s. ad | 1.0 ml. |

EXAMPLE 1

16α-METHYL-1,3,5(10),6,8,14-19-NOR-PREGNAHEXAENE-3,17α,21-TRIOL-20-ONE 21-ACETATE

A.
16α-Methyl-1,3,5(10),6,8,-19-Nor-Pregnapentaene-3,17α,21-Triol-20-One 21-Acetate To a refluxing solution of lithium chloride (120 gms.) and concentrated hydrochloric acid (1.8 ml.) in dimethylformamide (750 ml.) add 9α,11β-dichloro-16α-methyl-1,4-pregnadiene-17α,21-diol-3,20-dione 21-acetate (30 gms.). Heat the reaction mixture at reflux temperature for 15 minutes, then pour into water/ice (6 liters). Extract the aqueous mixture with ethyl acetate, wash the combined extracts with water, then evaporate to a volume of about 350 ml. Separate the resultant crystalline precipitate by filtration, wash the precipitate with ethyl acetate and air dry to obtain 16α-methyl-1,3,5(10),6,8-19-nor-pregnapentaene-3,17α,21-triol-20-one 21-acetate (yield 9.6 gms.); m.p. 235°–240° C., $[\alpha]_D^{26}+101°$ (dioxane), $\lambda_{max}^{methanol}$ 230 ($\epsilon=81,100$), 258 ($\epsilon=3600$), 269 ($\epsilon=4900$), 280 ($\epsilon=5600$), 292 ($\epsilon=4100$), 326 ($\epsilon=2400$), 346 nm ($\epsilon=800$).

B.
16α-Methyl-1,3,5(10),6,8,14-19-Nor-Pregnahexaene-3,17α,21-Triol-20-One 21-Acetate To a solution of 16α-methyl-1,3,5(10),6,8-19-nor-pregnapentaene-3,17α,21-triol-20-one 21-acetate (14.0 gms.) in dioxane (2 liters) add 2,3-dichloro-5,6-dicyanobenzoquinone (DDQ) (9.98 gms., 1.2 equivalents) and stir the reaction mixture at room temperature for 4½ hours. Separate the precipitated solids by filtration and wash the precipitate with dioxane. Combine the filtrate and washings and evaporate to a small volume. Dissolve the residue in ethyl acetate, wash the ethyl acetate solution with water, aqueous sodium bicarbonate solution, saturated sodium chloride solution and then with water. Evaporate the ethyl acetate solution in vacuo to a small volume and separate the resultant precipitate by filtration to obtain 16α-methyl-1,3,5(10),6,8,14-19-nor-pregnahexaene-3,17α,21-triol-20-one 21-acetate (yield 6.48 gms.). Concentrate the filtrate to dryness, triturate the resultant residue with ether and filter to obtain additional 16α-methyl-1,3,5(10),6,8,14-19-nor-pregnahexaene-3,17α,21-triol-20-one 21-acetate (yield 4.47 gms.), $[\alpha]_D^{26}-95°$ (dioxane), m.p. 218°–221° C.; $\lambda_{max}^{methanol}$ 248 ($\epsilon=36,000$), 257 ($\epsilon=46,400$), 266 ($\epsilon=49,200$), 288 sh ($\epsilon=13,900$), 298 ($\epsilon=19,000$), 310 nm ($\epsilon=17,900$).

EXAMPLE 2

OTHER 1,3,5(10),6,8,14-19-NOR-PREGNAHEXAENE-3,17α,21-TRIOL-20-ONE DERIVATIVES

A.
1,3,5(10),6,8,-19-Nor-Pregnapentaene-3,17α,21-Triol-20-One Derivatives

In a manner similar to that described in Example 1A, treat each of the following 9α,11β-dihalogeno-1,4-pregnadienes with lithium chloride in dimethylformamide.

(1) 9α,11β-dichloro-16β-methyl-1,4-pregnadiene-17α,21-diol-3,20-dione 21-acetate,
(2) 9α,11β-dichloro-16α-methyl-1,4-pregnadiene-17α,21-diol-3,20-dione 17,21-di-n-butyrate,
(3) 9α,11β-dichloro-1,4-pregnadiene-17α,21-diol-3,20-dione 21-acetate.

Isolate and purify each of the resultant products in a manner similar to that described in Example 1A to obtain, respectively,
(1) 16β-methyl-1,3,5(10),6,8-19-nor-pregnapentaene-3,17α,21-triol-20-one 21-acetate; m.p. 182°–184° C., $[\alpha]_D^{26}+122°$ (chloroform), $\lambda_{max}^{methanol}$ 229 ($\epsilon=67,000$), 258 ($\epsilon=3,700$), 268 ($\epsilon=4,800$), 279 ($\epsilon=5,500$), 291 ($\epsilon=4,000$), 327 ($\epsilon=2,400$), 340 nm ($\epsilon=2,700$).

(2) 16α-methyl-1,3,5(10),6,8-19-nor-pregnapentaene-3,17α,21-triol-20-one 17,21-di-n-butyrate; m.p. 200°–202°·C., $[\alpha]_D^{26} - 15°$ (dioxane), $\lambda_{max}^{methanol}$ 228 ($\epsilon = 67,000$), 257 ($\epsilon = 4,000$), 268 ($\epsilon = 5,100$), 279 ($\epsilon = 5,700$), 290 ($\epsilon = 4,000$), 325 ($\epsilon = 2,300$), 340 nm ($\epsilon = 2,700$).

(3) 1,3,5(10),6,8-19-nor-pregnapentaene-3,17α,21-triol-20-one 21-acetate; m.p. 185°–190° C., $[\alpha]_D^{26} + 91°$ (chloroform), $\lambda_{max}^{methanol}$, 229 ($\epsilon = 66,400$), 258 ($\epsilon = 3,600$), 268 ($\epsilon = 4,900$), 281 ($\epsilon = 5,700$), 291 ($\epsilon = 4,200$), 327 ($\epsilon = 2,600$), 340 nm ($\epsilon = 3,100$).

B. In a manner similar to that described in Example 1B, treat each of the 1,3,5(10),6,8-19-nor-pregnapentaenes prepared in Example 2A with DDQ in dioxane and isolate and purify each of the resultant products in a manner similar to that described to obtain, respectively, (1) 16β-methyl-1,3,5(10),6,8,14-19-nor-pregnahexaene-3,17α,21-triol-20-one 21-acetate; m.p. 177°–179° C., $[\alpha]_D^{26} + 95°$ (chloroform) $\lambda_{max}^{methanol}$ 253 ($\epsilon = 51,300$), 262 ($\epsilon = 51,800$), 284 ($\epsilon = 13,400$), 295 ($\epsilon = 18,100$), 306 ($\epsilon = 16,800$), 327 ($\epsilon = 2,800$), 354 nm ($\epsilon = 1,700$).

(2) 16α-methyl-1,3,5(10),6,8,14-19-nor-pregnahexaene-3,17α,21-triol-20-one 17,21-di-n-butyrate; m.p. 188°–190° C., $[\alpha]_D^{26} - 201°$ (chloroform), $\lambda_{max}^{methanol}$ 246 ($\epsilon = 38,700$), 255 ($\epsilon = 51,300$), 264 ($\epsilon = 51,300$), 287 ($\epsilon = 15,300$), 297 ($\epsilon = 20,000$), 309 ($\epsilon = 18,700$), 339 ($\epsilon = 2,000$), 355 nm ($\epsilon = 1,500$).

(3) 1,3,5(10),6,8,14-19-nor-pregnahexaene-3,17α,21-triol-20-one 21-acetate; m.p. 212°–216° C., $[\alpha]_D^{26} - 30°$ (dioxane), $\lambda_{max}^{methanol}$ 245 ($\epsilon = 38,000$), 253 ($\epsilon = 49,900$), 262 ($\epsilon = 46,700$), 286 ($\epsilon = 13,300$), 295 ($\epsilon = 17,900$), 307 ($\epsilon = 16,500$), 338 ($\epsilon = 2,000$), 355 nm ($\epsilon = 1,600$).

EXAMPLE 3

3-ALKOXY DERIVATIVES OF 1,3,5(10),6,8,14-19-NOR-PREGNAHEXAENE-3,17α,21-TRIOL-20-ONES

A.
3-Methoxy-16α-Methyl-1,3,5(10),6,8,14-19-Nor-Pregnahexaene-17α,21-Diol-20-One 21-Acetate To a solution of 16α-methyl-1,3,5(10),6,8,14-19-nor-pregnahexaene-3,17α,21-triol-20-one 21-acetate (1 gm.) in ethyl acetate (50 ml.), add a solution of diazomethane in ether (molar quantity of diazomethane being greater than that of pregnahexaene). Allow the reaction mixture to stand overnight at room temperature, then distill the excess diazomethane and ether. Purify the resultant residue via chromatography on silica gel preparative plates utilizing as solvent system chloroform:ethyl acetate (4:1). Remove the band containing the desired product as visualized under ultraviolet light by extraction with ethyl acetate. Evaporate the ethyl acetate and crystallize the resultant residue from petroleum ether:ether to obtain 3-methoxy-16α-methyl-1,3,5(10),6,8,14-19-nor-pregnahexaene-17α,21-diol-20-one 21-acetate, yield = 230 mg.; m.p. 186°–188° C.; $[\alpha]_D^{26} - 109°$ (chloroform); $\lambda_{max}^{methanol}$ 246 ($\epsilon = 36,600$), 254 ($\epsilon = 46,300$), 264 ($\epsilon = 47,000$), 283 ($\epsilon = 14,700$), 293 ($\epsilon = 20,200$), 306 ($\epsilon = 19,700$), 335 ($\epsilon = 1,700$), 352 nm ($\epsilon = 1,300$).

B. In similar manner, treat each of the 3-hydroxy-1,3,5(10),6,8,14-19-nor-pregnahexaenes of Example 2B with diazo-methane to obtain, respectively, (1) 3-methoxy-16β-methyl-1,3,5(10),6,8,14-19-nor-pregnahexaene-17α,21-diol-20-one 21-acetate, (2) 3-methoxy-16α-methyl-1,3,5(10),6,8,14-19-nor-pregnahexaene-17α,21-diol-20-one 17,21-di-n-butyrate, and (3) 3-methoxy-1,3,5(10),6,8,14-19-nor-pregnahexaene-17α,21-diol-20-one 21-acetate.

C. In the procedures of Examples 3A and 3B, by substituting for diazomethane other diazoalkane solutions, e.g. diazoethane, there is obtained the corresponding 3-alkoxy derivative, e.g. the 3-ethoxy derivatives corresponding to the 3-methoxy products of Examples 3A and 3B.

EXAMPLE 4

1,3,5(10),6,8,14-19-NOR-PREGNAHEXAENE-3,17α,21-TRIOL-20-ONE AND 16-METHYL DERIVATIVES THEREOF

A.
16α-Methyl-1,3,5(10),6,8,14-19-Nor-Pregnahexaene-3,17α,21-Triol-20-One

To a solution of 16α-methyl-1,3,5(10),6,8,14-19-nor-pregnahexaene-3,17α,21-triol-20-one 21-acetate (1 gm.) in methanol (70 ml.) under an atmosphere of nitrogen, add aqueous sodium bicarbonate (10%, 5 ml.). Heat at reflux temperature for 30 minutes, cool, add dilute acetic acid until the reaction mixture is at about pH 7, pour into water and extract with ethyl acetate. Wash the combined extracts with water, dry over magnesium sulfate, and evaporate. Crystallize the resultant residue from chloroform: ethyl acetate to obtain 16α-methyl-1,3,5(10),6,8,14-19-nor-pregnahexaene-3,17α,21-triol-20-one, yield = 697 mg., $[\alpha]_D^{26} - 188°$ (dioxane), m.p. 220°–225° C., $\lambda_{max}^{methanol}$ 246 ($\epsilon = 35,000$), 255 ($\epsilon = 45,100$), 264 ($\epsilon = 45,900$), 285 ($\epsilon = 13,800$), 296 ($\epsilon = 18,500$), 308 ($\epsilon = 17,900$), 338 ($\epsilon = 2,600$), 355 nm ($\epsilon = 1,700$).

B. In similar manner, treat each of 16β-methyl-1,3,5(10),6,8,14-19-nor-pregnahexaene-3,17α,21-triol-20-one 21-acetate and 1,3,5(10),6,8,14-19-nor-pregnahexaene-3,17α,21-triol-20-one 21-acetate with aqueous sodium bicarbonate and isolate and purify the resultant products in the described manner to obtain, respectively, 16β-methyl-1,3,5(10),6,8,14-19-nor-pregnahexaene-3,17α,21-triol-20-one and 1,3,5(10),6,8,14-19-nor-pregnahexaene-3,17α,21-triol-20-one.

EXAMPLE 5

PREPARATION OF 17-MONO-LOWER ALKANOATES AND 21-MONO-LOWER ALKANOATES FROM THE CORRESPONDING 1,3,5(10),6,8,14-19-NOR-PREGNAHEXAENE-3,17α,21-TRIOL-20-ONE

A. The 21-Propionate and the 17-Propionate of 16α-Methyl-1,3,5(10),6,8,14-19-Nor-Pregnahexaene-3,17α,21-Triol-20-One To a solution of 16α-methyl-1,3,5(10),6,8,14-19--nor-pregnahexaene-3,17α,21-triol-20-one (697 mg.) in dimethylsulfoxide (9.7 ml.), add triethylorthopropionate (0.97 ml.) and p-toluene sulfonic acid (97 mg.). Stir the reaction mixture at room temperature for 5 hours, then add acetic acid/water (14 ml., 9:1) and stir the mixture at room temperature overnight. Pour the reaction mixture into water and separate the resultant precipitate by filtration and wash the precipitate with water. Chromatograph the precipitate over silica gel eluting with methylene chloride/ether (19:1), and combine the like early fractions as determined by thin layer chromatography, evaporate and crystallize the resultant residue from ether and filter to obtain 16α-methyl-1,3,5(10),6,8,14-19-nor-pregnahexaene-3,17α,21-triol-20-one 21-propionate, yield=138 mg., m.p. 218°-222° C., $[\alpha]_D^{26} -109°$ (chloroform), $\lambda_{max}^{methanol}$, 246 ($\epsilon=36,500$), 255 ($\epsilon=47,400$), 264 ($\epsilon=48,200$), 286 ($\epsilon=13,900$), 296 ($\epsilon=19,300$), 309 ($\epsilon=18,200$), 338 ($\epsilon=2,000$), 355 nm ($\epsilon=1,500$).

Continue eluting with the same solvent and combine the like later fractions as determined by thin layer chromatography, evaporate and crystallize the resultant precipitate from ether/petroleum ether and filter to obtain 16α-methyl-1,3,5(10),6,8,14-19-nor-pregnahexaene-3,17α,21-triol-20-one 17-propionate, yield=41 mg., m.p. 115°-120° C., $[\alpha]_D^{26} -212°$ (chloroform).

B. In similar manner, treat each of 16β-methyl-1,3,5(10),6,8,14-19-nor-pregnahexaene-3,17α,21-triol-20-one and 1,3,5(10),6,8,14-19-nor-pregnahexaene-3,17α,21-triol-20-one with triethylorthopropionate and p-toluenesulfonic acid, followed by treatment with aqueous acetic acid, and isolate and purify each of the resultant products in a manner similar to that described hereinabove to obtain, respectively, 16β-methyl-1,3,5(10),6,8,14-19-nor-pregnahexaene-3,17α,21-triol-20-one 21-propionate and 16β-methyl-1,3,5(10),6,8,14-19-nor-pregnahexaene-3,17α,21-triol-20-one 17-propionate, 1,3,5(10),6,8,14-19-nor-pregnahexaene-3,17α,21-triol-20-one 21-propionate and 1,3,5(10),6,8,14-19-nor-pregnahexaene-3,17α,21-triol-20-one 17-propionate.

EXAMPLE 6

15-CHLORO-1,3,5(10),6,8,14-19-NOR-PREGNAHEXAENE-3,17α,21-TRIOL-20-ONES

A.

15-Chloro-16α-Methyl-1,3,5(10),6,8,14-19-Nor-Pregnahexaene-3,17α,21-Triol-20-One 21-Acetate To a saturated solution of hydrogen chloride gas in dioxane (50 ml.), add 16α-methyl-1,3,5(10),6,8-19-nor-pregnapentaene-3,17α,21-triol-20-one 21-acetate (382 mg.), (warm slightly to dissolve). To this solution add 2,3-dichloro-5,6-dicyanobenzoquinone (DDQ) (454 mg.) and stir the reaction mixture at room temperature for 30 minutes. Evaporate the dioxane, dissolve the resultant residue in ether and percolate the ether solution through an alumina column. Evaporate the combined eluates and chromatograph the resultant residue over silica gel eluting with petroleum ether/ether gradient elution. Combine the like fractions containing the desired product as determined by thin layer chromatography, evaporate the combined eluates and recrystallize the resultant residue from ether/petroleum ether and filter the resultant precipitate to give 15-chloro-16α-methyl-1,3,5(10),6,8,14-19-nor-pregnahexaene-3,17α,21-triol-20-one 21-acetate, yield=131 mg, m.p. 225°-228° C., $[\alpha]_D^{26} -185°$ (chloroform), $\lambda_{max}^{methanol}$ 258 ($\epsilon=44,700$), 266 ($\epsilon=49,200$), 290 ($\epsilon=12,500$), 303 ($\epsilon=15,000$), 315 ($\epsilon=14,600$), 336 ($\epsilon=3,900$), 354 nm ($\epsilon=2,900$).

B. In similar manner, treat each of the 19-nor-pregnapentaenes prepared in Example 2A with DDQ and hydrogen chloride, and isolate and purify each of the resultant products in a manner similar to that described hereinabove to obtain, respectively, (1) 15-chloro-16β-methyl-1,3,5(10),6,8,14-19-nor-pregnahexaene-3,17α,21-triol-20-one 21-acetate, (2) 15-chloro-16α-methyl-1,3,5(10),6,8,14-19-nor-pregnahexaene-3,17α,21-triol-20-one 17,21-di-n-butyrate, (3) 15-chloro-1,3,5(10),6,8,14-19-nor-pregnahexaene-3,17α,21-triol-20-one 21-acetate.

EXAMPLE 7

PREPARATION OF 3-HYDROCARBONCARBOXYLATE ESTERS

A.

16α-Methyl-1,3,5(10),6,8,14-19-Nor-Pregnahexaene-3,17α,21-Triol-20-one 3,21-Diacetate To a solution of 16α-methyl-1,3,5(10),6,8,14-19-nor-pregnahexaene-3,17α,21-triol-20-one 21-acetate (450 mg.) in pyridine (2 ml.) add acetic anhydride (1 ml.) and allow the reaction mixture to stand at room temperature overnight. Pour the reaction mixture into dilute hydrochloric acid, separate the resultant precipitate by filtration, wash the precipitate with water, dry and crystallize from ether to obtain 16α-methyl-1,3,5(10),6,8,14-19-nor-pregnahexaene-3,17α,21-triol-20-one 3,21-diacetate, yield=232 mg., m.p. 153°-157° C., $[\alpha]_D^{26} -93°$ (chloroform); $\lambda_{max}^{methanol}$ 388 ($\epsilon=29,300$), 246 ($\epsilon=32,600$), 255 ($\epsilon=41,360$), 264 ($\epsilon=41,600$), 283 ($\epsilon=14,500$), 293 ($\epsilon=18,000$), 306 ($\epsilon=16,700$), 330 nm ($\epsilon=600$).

B.

16α-Methyl-1,3,5(10),6,8,14-19-Nor-Pregnahexaene-3,17α,21-Triol-20-one 3-Benzoate 21-Acetate In the procedure of Example 7A, by substituting for acetic anhydride an equivalent quantity of benzoyl chloride, three is obtained 16α-methyl-1,3,5(10),6,8,14-19-nor-pregnahexaene-3,17α,21-triol-20-one 3-benzoate 21-acetate, m.p. 197°-202° C., $[\alpha]_D^{26} -68°$ (chloroform), $\lambda_{max}^{methanol}$ 238 ($\epsilon=39,300$), 256 ($\epsilon=44,800$), 265 ($\epsilon=45,500$), 283 ($\epsilon=16,000$), 295 ($\epsilon=17,900$), 307 nm ($\epsilon=17,000$).

C. In similar manner treat each of the 3-hydroxy- or 3,21-dihydroxy-1,3,5(10),6,8,14-19-nor-pregnahexaene compounds prepared in Examples 2, 5 and 6 with acetic anhydride in pyridine or benzoyl chloride in pyridine to obtain the corresponding 3-acetate or 3-benzoate ester thereof, or the corresponding 3,21-diacetate or 3,21-dibenzoate, respectively.

D. Treat each of the 3,17α,21-trihydroxy-1,3,5(10),6,8,14-19-nor-pregnahexaenes prepared in Example 4 with acetic anhydride in pyridine or benzoyl chloride in pyridine according to procedures of above Examples 7A and 7B to obtain, respectively, (1) 16α-methyl-1,3,5(10),6,8,14-19-nor-pregnahexaene-3,17α,21-triol-20-one 3,21-diacetate, (2) 16α-methyl-1,3,5(10),6,8,14-19-nor-pregnahexaene-3,17α,21-triol-20-one 3,21-dibenzoate, (3) 16β-methyl-1,3,5(10),6,8,14-19-nor-pregnahexaene-3,17α,21-triol-20-one 3,21-diacetate, (4) 16β-methyl-1,3,5(10),6,8,14-19-nor-pregnahexaene-3,17α,21-triol-20-one 3,21-dibenzoate, (5) 1,3,5(10),6,8,14-19-nor-pregnahexaene-3,17α,21-triol-20-one 3,21-diacetate, (6) 1,3,5(10),6,8,14-19-nor-pregnahexaene-3,17α,21-triol-20-one 3,21-dibenzoate.

EXAMPLE 8

OTHER 1,3,5(10),6,8,14-19-NOR-PREGNAHEXAENE-3,17α,21-TRIOL-20-ONES

A. Other 1,3,5(10),6,8-19-Nor-Pregnapentaene-3,17α,21-Triol-20-Ones

In a manner similar to that described in Example 1A, treat each of the following 9α,11β-dihalogeno-1,4-pregnadienes with lithium chloride in dimethylformamide.

(1) 6α,16α-dimethyl-9α,11β-dichloro-1,4-pregnadiene-17α,21-diol-3,20-dione 21-acetate,
(2) 6α-fluoro-9α,11β-dichloro-1,4-pregnadiene-17α,21-diol-3,20-dione 21-acetate,
(3) 6α-fluoromethyl-9α,11β-dichloro-1,4-pregnadiene-17α,21-diol-3,20-dione 21-acetate,
(4) 6α-difluoromethyl-9α,11β-dichloro-1,4-pregnadiene-17α,21-diol-3,20-dione 21-acetate,
(5) 6α-trifluoromethyl-9α,11β-difluoro-1,4-pregnadiene-17α,21-diol-3,20-dione 21-acetate,
(6) 9α,11β-dichloro-1,4-pregnadiene-16α,17α,21-triol-3,20-dione 16,21-diacetate,
(7) 6α-fluoro-9α,11β-dichloro-16α,17α-isopropylidenedioxy-1,4-pregnadiene-21-ol-3,20-dione 21-acetate,
(8) 6α-fluoro-9α,11β-dichloro-16α-methyl-1,4-pregnadiene-17α,21-diol-3,20-dione 21-acetate,
(9) 6α-methyl-9α,11β-dichloro-1,4-pregnadiene-17α,21-diol-3,20-dione 21-acetate,
(10) 6α,16β-dimethyl-9α,11β-dichloro-1,4-pregnadiene-17α,21-diol-3,20-dione 21-acetate.

Isolate and purify each of the resultant products in a manner similar to that described to obtain, respectively,
(1) 6,16α-dimethyl-1,3,5(10),6,8-19-nor-pregnapentaene-3,17α,21-triol-20-one 21-acetate,
(2) 6-fluoro-1,3,5(10),6,8-19-nor-pregnapentaene-3,17α,21-triol-20-one 21-acetate,
(3) 6-fluoromethyl-1,3,5(10),6,8-19-nor-pregnapentaene-3,17α,21-triol-20-one 21-acetate,
(4) 6-difluoromethyl-1,3,5(10),6,8-19-nor-pregnapentaene-3,17α,21-triol-20-one 21-acetate,
(5) 6-trifluoromethyl-1,3,5(10),6,8-19-nor-pregnapentaene-3,17α,21-triol-20-one 21-acetate,
(6) 1,3,5(10),6,8-19-nor-pregnapentaene-3,16α,17α,21-tetrol-20-one 16,21-diacetate,
(7) 6-fluoro-16α,17α-isopropylidenedioxy-1,3,5(10),6,8-19-nor-pregnapentaene-3,21-diol-20-one 21-acetate,
(8) 6-fluoro-16α-methyl-1,3,5(10),6,8-19-nor-pregnapentaene-3,17α,21-triol-20-one 21-acetate,
(9) 6-methyl-1,3,5(10),6,8-19-nor-pregnapentaene-3,17α,21-triol-20-one 21-acetate,
(10) 6,16β-dimethyl-1,3,5(10),6,8-19-nor-pregnapentaene-3,17α,21-triol-20-one 21-acetate.

B. In a manner similar to that described in Example 1B, treat each of the 1,3,5(10),6,8-19-nor-pregnapentaenes prepared in Example 8A with DDQ in dioxane and isolate and purify each of the resultant products in a manner similar to that to obtain, respectively,
(1) 6,16α-dimethyl-1,3,5(10),6,8,14-19-nor-pregnahexaene-3,17α,21-triol-20-one 21-acetate,
(2) 6-fluoro-1,3,5(10),6,8,14-19-nor-pregnahexaene-3,17α,21-triol-20-one 21-acetate,
(3) 6-fluoromethyl-1,3,5(10),6,8,14-19-nor-pregnahexaene-3,17α,21-triol-20-one 21-acetate,
(4) 6-difluoromethyl-1,3,5(10),6,8,14-19-nor-pregnahexaene-3,17α,21-triol-20-one 21-acetate,
(5) 6-trifluoromethyl-1,3,5(10),6,8,14-19-nor-pregnahexaene-3,17α,21-triol-20-one 21-acetate,
(6) 1,3,5(10),6,8,14-19-nor-pregnahexaene-3,16α,17α21-tetrol-20-one 16,21-diacetate,
(7) 6-fluoro-16α,17α-isopropylidenedioxy-1,3,5(10),6,8,14-19-nor-pregnahexaene-3,21-diol-20-one 21-acetate,
(8) 6-fluoro-16α-methyl-1,3,5(10),6,8,14-19-nor-pregnahexaene-3,17α,21-triol-20-one 21-acetate,
(9) 6-methyl-1,3,5(10),6,8,14-19-nor-pregnahexaene-3,17α,21-triol-20-one 21-acetate,
(10) 6,16β-dimethyl-1,3,5(10),6,8,14-19-nor-pregnahexaene-3,17α,21-triol-20-one 21-acetate.

EXAMPLE 9

16α-METHYL-1,3,5(10),6,8,14-19-NOR-PREGNAHEXAENE-3,17α,21-TRIOL-11,20-DIONE 3-BENZOATE 21-ACETATE

A. 16α-Methyl-1,3,5(10),6,8-19-Nor-Pregnapentaene-3,17α,21-Triol-11,20-Dione 3-Benzoate 21-Acetate To a solution of 9α-bromo-16α-methyl-1,4-pregnadiene-17α,21-diol-3,11,20-trione 21-acetate (30 gms.) in pyridine (240 ml.) add benzoyl chloride (60 ml.) and heat the reaction mixture at 60° C. for 20 hours, cool and pour into dilute hydrochloric acid. Extract the aqueous solution with ethyl acetate, wash the combined extracts with water, and evaporate. Chromatograph the resultant residue over silica gel eluting with petroleum ether/ether gradient. Combine the like fractions containing the desired product as determined by thin layer chromatography, evaporate, then crystallize the resultant residue from ether to obtain 16α-methyl-1,3,5(10),6,8-19-nor-pregnapentaene-3,17α,21-triol-11,20-dione 3-benzoate 21-acetate, yield 13.1 gms.; m.p. 183°–184°; $[\alpha]_D^{26}+63°$ (dioxane); $\lambda_{max}^{methanol}$ 215 ($\epsilon=40,600$), 237 ($\epsilon=38,400$), 314 nm ($\epsilon=7,900$).

B. 16α-Methyl-1,3,5(10),6,8,14-19-Nor-Pregnahexaene-3,17α,21-Triol-11,20-Dione 3-Benzoate 21-Acetate To a solution of 16α-methyl-1,3,5(10),6,8-19-nor-pregnapentaene-3,17α,21-triol-11,20-dione 3-benzoate 21-acetate (10.4 gms.) in dioxane (500 ml.) add DDQ (13.33 gms., 2.4 eq.) and heat the reaction mixture at reflux temperature for 48 hours. Evaporate the reaction mixture in vacuo, dissolve the resultant residue in methylene chloride and percolate through alumina (Activity V). Evaporate the combined eluates to a small volume and chromatograph over silica gel eluting with petroleum ether/ether gradient. Combine the like fractions containing the desired product as determined by thin layer chromatography, and evaporate, then recrystallize the resultant residue from ether to obtain 16α-methyl-1,3,5(10),6,8,14-19-nor-pregnahexaene-3,17α,21-triol-11,20-dione 3-benzoate 21-acetate; m.p. 144°–145° C.; $[\alpha]_D^{26}+1°$ (dioxane); $\lambda_{max}^{methanol}$ 234 ($\epsilon=37,700$), 270 ($\epsilon=42,900$), 277 sh ($\epsilon=40,400$), 312 ($\epsilon=9,000$), 349 ($\epsilon=6,000$) and 365 nm ($\epsilon=5,300$).

EXAMPLE 10

16α-METHYL-1,3,5(10),6,8,14-19-NOR-PREGNAHEXAENE-3,17α,21-TRIOL-11,20-DIONE

To a solution of 16α-methyl-1,3,5(10),6,8,14-19-nor-pregnahexaene-3,17α,21-triol-11,20-dione 3-benzoate 21-acetate (5 gms.) in methanol (250 ml.) add sodium bicarbonate (25 ml. of a 10% aqueous solution) and heat the reaction mixture at reflux temperature under an atmosphere of nitrogen for 2 hours. Cool the reaction mixture, evaporate the methanol in vacuo, dissolve the resultant residue in ethyl acetate, wash the ethyl acetate solution with water, then evaporate. Chromatograph the resultant residue over silica gel eluting with petroleum ether/ether gradient. Combine the like fractions containing the desired product as determined by thin layer chromatography and evaporate, then crystallize the resultant residue from ethyl acetate to obtain 16α-methyl-1,3,5(10),6,8,14-19-nor-pregnahexaene-3,17α,21-triol-11,20-dione; m.p. 163°–165° C.; $[\alpha]_D^{26} -107°$ (dioxane); $\lambda_{max}^{methanol}$ 236 ($\epsilon=24,100$), 276 ($\epsilon=34,000$), 317 ($\epsilon=5,600$), and 378nm ($\epsilon=5,700$).

EXAMPLE 11

OTHER ESTER DERIVATIVES OF 16α-METHYL-1,3,5(10),6,8,14-19-NOR-PREG-NAHEXAENE-3,17α,21-TRIOL-11,20-DIONE

A. The 21-Propionate and the 17-Propionate of 16α-Methyl-1,3,5(10),6,8,14-19-Nor-Pregnahexaene-3,17α,21-Triol-11,20-Dione To a solution of 16α-methyl-1,3,5(10),6,8,14-19-nor-pregnahexaene-3,17α,21-triol-11,20-dione (100 mg.) in dimethylsulfoxide (1.4 ml.) add triethylorthopropionate (0.14 ml.) and p-toluenesulfonic acid (14 mg.). Stir at room temperature for 5 hours, then add acetic acid/water (2 ml.; 9:1) and continue stirring the reaction mixture for 20 hours. Pour the reaction mixture into aqueous sodium bicarbonate, extract with ethyl acetate, wash the combined extracts with water, then evaporate in vacuo. Chromatograph the resultant residue on 2×1000 mμ silica gel GF plates using a chloroform/ethyl acetate (3:1) solvent system. Visualize the plate under ultraviolet light and extract separately each of the two steroidal bands with ethyl acetate, and evaporate to residues yielding, respectively, 16α-methyl-1,3,5(10),6,8,14-19-nor-pregnahexaene-3,17α,21-triol-11,20-dione 21-propionate (25 mgs.; the residue from the least polar band), and 16α-methyl-1,3,5(10),6,8,14-19-nor-pregnahexaene-3,17α,21-triol-11,20-dione 17-propionate (25 mgs.; the residue from the most polar band).

B.
16α-Methyl-1,3,5(10),6,8,14-19-Nor-Pregnahexaene-3,17α,21-Triol-11,20-Dione 3,17,21-Tripropionate To a suspension of 16α-methyl-1,3,5(10),6,8,14-19-nor-pregnahexaene-3,17α,21-triol-11,20-dione (2 gms.) in propionic acid (20 ml.) containing p-toluenesulfonic acid (200 mg.) at −5° C., add dropwise over a 40-minute period trifluoroacetic anhydride (8 ml.). Allow the reaction mixture to warm to room temperature, then stir for 24 hours. Pour the reaction mixture onto ice/-water and extract with ethyl acetate. Wash the combined extracts with aqueous sodium bicarbonate, then with water and evaporate in vacuo. Chromatograph the resultant residue over silica gel eluting with petroleum ether/ether gradient. Combine the like fractions containing the desired product as determined by thin layer chromatography to obtain 16α-methyl-1,3,5(10),6,8,14-19-nor-pregnahexaene-3,17α,21-triol-11,20-dione 3,17,21-tripropionate; yield 2.04 gms.; $[\alpha]_D^{26} -82°$ (dioxane); $\lambda_{max}^{methanol}$ 233 ($\epsilon=26,300$), 260 sh ($\epsilon=30,700$), 269 ($\epsilon=36,100$), 278 ($\epsilon=34,800$), 316 ($\epsilon=7,700$), 345 sh ($\epsilon=5,400$), 364 nm ($\epsilon=4,600$).

C.
16α-Methyl-1,3,5(10),6,8,14-19-Nor-Pregnahexaene-3,17α,21-Triol-11,20-Dione 3,21-Diacetate To 16α-methyl-1,3,5(10),6,8,14-19-nor-pregnahexaene-3,17α,21-triol-11,20-dione (460 mg.) in pyridine (20 ml.) add acetic anhydride (2 ml.) and allow the reaction mixture to stay at room temperature for 4 hours. Pour the reaction mixture into dilute hydrochloric acid, extract with ethyl acetate, wash the combined extracts with water and evaporate in vacuo. Chromatograph the resultant residue over silica gel eluting with petroleum ether/ether gradient. Combine the like eluates as determined by thin layer chromatography to obtain 16α-methyl-1,3,5(10),6,8,14-19-nor-pregnahexaene-3,17α,21-triol-11,20-dione 3,21-diacetate; $[\alpha]_D^{26} -1°$ C. (dioxane); $\lambda_{max}^{methanol}$ 234 ($\epsilon=25,900$), 269 ($\epsilon=33,300$), 278 ($\epsilon=29,300$), 315 ($\epsilon=7,800$), 348 ($\epsilon=5,300$) and 365 nm ($\epsilon=4,700$)

D.
16α-Methyl-1,3,5(10),6,8,14-19-Nor-Pregnahexaene-3,17α,21-Triol-11,20-Dione 3,21-Dipropionate In the procedure of Example 11C, by utilizing an equivalent quantity of propionic anhydride instead of acetic anhydride there is obtained 16α-methyl-1,3,5(10),6,8,14-19-nor-pregnahexaene-3,17α,21-triol-11,20-dione 3,21-dipropionate; m.p. 135°–137° C.; $\lambda_{max}^{methanol}$ 233 ($\epsilon=24,000$), 269 ($\epsilon=32,700$), 279 sh ($\epsilon=28,500$), 315 ($\epsilon=7,100$), 349 ($\epsilon=5,000$) and 365 nm ($\epsilon=4,300$); $[\alpha]_D^{26} +2°$ (dioxane).

EXAMPLE 12

16α-METHYL-1,3,5(10),6,8,14-19-NOR-PREG-NAHEXAENE-3,11β,17α,21-TETROL-20-ONE 3,17,21-TRIPROPIONATE AND 17,21-DIPROPIONATE

To a solution of 16α-methyl-1,3,5(10),6,8,14-19-nor-pregnahexaene-3,17α,21-triol-11,20-dione 3,17,21-tripropionate (1 gm.) in tetrahydrofuran/methanol (50 ml., 1:1) (dried over an alumina column) at 0° C. add sodium borohydride (220 mg., 3 eq.) portionwise over a 5-minute period. Stir the reaction mixture for an additional 10 minutes, then bring to neutrality by adding glacial acetic acid dropwise. Pour the reaction mixture into water, extract with ethyl acetate, wash the combined extracts with water and evaporate. Chromatograph the resultant residue over silica gel GF column eluting with chloroform/ethyl acetate (9:1). Combine the like fractions as determined by thin layer chromatography, and evaporate each of the three different combined fractions to residues comprising, respectively, (1) 16α-methyl-1,3,5(10),6,8,14-19-nor-pregnahexaene-3,11α,17α,21-tetrol-20-one 3,17α,21-tripropionate (yield 53 mg.);

(2) 16α-methyl-1,3,5(10),6,8,14-19-nor-pregnahexaene-3,11β,17α,21-tetrol-20-one 3,17α,21-tripropionate. Purify by recrystallization from petroleum ether/ether; $[\alpha]_D^{26} -136°$ C. (dioxane); $\lambda_{max}^{methanol}$ 237 ($\epsilon=30,200$), 244 ($\epsilon=34,000$), 253 ($\epsilon$-45,100), 262 ($\epsilon=44,200$), 281 ($\epsilon=16,200$), 291 ($\epsilon=20,300$), 304 ($\epsilon=18,500$), 328 ($\epsilon=900$), and 344 nm ($\epsilon=500$); yield=502 mg.

(3) 16α-methyl-1,3,5(10),6,8,14-19-nor-pregnahexaene-3,11β,17α,21-tetrol-20-one 17,21-dipropionate. Purify by recrystallizing from petroleum ether/ether;

$[\alpha]_D^{26}$ −145° C. (dioxane); $\lambda_{max}^{methanol}$ 236 sh ($\epsilon$=28,100), 244 ($\epsilon$=33,800), 256 ($\delta$=40,200), 265 ($\epsilon$=40,200) 287 sh ($\delta$=12,600), 297 ($\delta$=16,400), 308 ($\delta$=15,500), 337 nm ($\delta$=2,700); yield=93 mg.

EXAMPLE 13

6-FLUORO-16α-METHYL-1,3,5(10),6,8,14-19-NOR-PREGNAHEXAENE-3,17α,21-TRIOL-20-ONE 21-ACETATE

A.

6-Fluoro-16α-Methyl-1,3,5(10),6,8-19-Nor-Pregnapentaene-3,17α,21-Triol-20-One 21-Acetate Add 6α-fluoro-9α,11β-dichloro-16α-methyl-1,4-pregnadiene-17α,21-diol-3,20-dione 21-acetate (4.2 gms.) to refluxing dimethylformamide (200 ml.) and continue heating at reflux temperature for 30 minutes. Pour the reaction mixture into saturated sodium chloride, separate the resultant precipitate by filtration. Dissolve the precipitate in ethyl acetate, and fractionally crystallize to obtain 6α-fluoro-16α-methyl-1,4,8(14),9(11)-pregnatetraene-17α,21-diol-3,20-dione 21-acetate and 6-fluoro-16α-methyl-1,3,5(10),6,8-19-nor-pregnapentaene-3,17α,21-triol-20-one 21-acetate. Further purify the latter compound by crystallization from methylene chloride, yield 316 mg., $[\alpha]_D^{26}$+88.0° (dioxane); m.p. 238°–241° C.; $\lambda_{max}^{methanol}$ 238 ($\epsilon$=50,500), 270 ($\epsilon$=5,000), 281 ($\epsilon$=5,000), 293 ($\epsilon$=3,400), 315 sh ($\epsilon$=1,700), 330 ($\epsilon$=2,400), 344 nm ($\epsilon$=2,600).

B.

6-Fluoro-16α-Methyl-1,3,5(10),6,8,14-19-Nor-Pregnahexaene-3,17α,21-Triol-20-One 21-Acetate Prepare a solution of 6-fluoro-16α-methyl-1,3,5(10),6,8-19-nor-pregnapentaene-3,17α,21-triol-20-one 21-acetate (200 mg.) in dioxane (10 ml.) containing DDQ (136 mg.), and stir at room temperature for 2 hours. Percolate the reaction mixture through alumina (activity V) eluting with ethyl acetate. Chromatograph the combined eluates over silica gel eluting with petroleum ether/ether gradient. Combine the like fractions containing the desired product as determined by thin layer chromatography, evaporate and crystallize the resultant product from petroleum ether/ether to obtain 6-fluoro-16α-methyl-1,3,5(10),6,8,14-19-nor-pregnahexaene-3,17α,21-triol-20-one 21-acetate, yield 35 mg; m.p. 200°–202° C.; $\lambda_{max}^{methanol}$ 248 sh ($\epsilon$=36,300); 255 ($\epsilon$=48,100); 265 ($\epsilon$=49,200); 288 ($\epsilon$=13,900); 299 ($\epsilon$=19,500); 311 ($\epsilon$=18,500); 342 ($\epsilon$=2,100); 359 nm ($\epsilon$=1,500).

EXAMPLE 14

16β-METHYL-1,3,5(10),6,8,14-19-NOR-PREGNAHEXAENE-3,11β,17α,21-TETROL-20-ONE 21-ACETATE

A.

16β-Methyl-1,4,6,8-Pregnatetraene-11β,17α,21-Triol-3,20-Dione 21-Acetate

To a mixture of 9α-chloro-16β-methyl-1,4,6-pregnatriene-11β,17α,21-triol-3,20-dione 21-acetate (3.44 gms.) in acetone (700 ml.) add potassium acetate (10.3 gms.) and reflux the reaction mixture with stirring for 48 hours. Filter the reaction mixture, evaporate the filtrate in vacuo to a low volume, pour into water and extract the aqueous mixture with ethyl acetate. Wash the combined organic extracts with water and evaporate to a volume of about 100 ml. Separate the resultant crystalline solid by filtration, and dry to obtain 16β-methyl-1,4,6,8-pregnatetraene-11β,17α,21-triol-3,20-dione 21-acetate, yield 1.96 gms; m.p. 175°–180° C.; $[\alpha]_D^{26}$+786° (pyridine); $\lambda_{max}^{methanol}$ 230 sh ($\epsilon$=10,600), 264 ($\epsilon$=10,000), 388 nm ($\epsilon$=6,500).

B.

16β-Methyl-1,3,5(10),6,8-19-Nor-Pregnapentaene-3,11β,17α,21-Tetrol-20-One 21-Acetate To a solution of 16β-methyl-1,4,6,8-pregnatetraene-11β,17α,21-triol-3,20-dione 21-acetate (850 mg.) in tetrahydrofuran (200 ml.) add 1 N hydrochloric acid (20 ml.). Stir the reaction mixture at room temperature for 1 hour, then pour the reaction mixture into 1 liter of saturated aqueous sodium chloride and extract with ethyl acetate. Wash the combined ethyl acetate extracts with water and evaporate to a volume of about 25 ml. Separate the resultant crystalline precipitate by filtration and dry to obtain 16β-methyl-1,3,5(10),6,8-19-nor-pregnapentaene-3,11β,17α,21-tetrol-20-one 21-acetate, yield 368 mg.; m.p. 203°–207° C.; $[\alpha]_D^{26}$+172° (pyridine); $\lambda_{max}^{methanol}$ 233 ($\epsilon$=69,100), 267 ($\epsilon$=4,800), 278 ($\epsilon$=5,400), 315 ($\epsilon$=1,900), 327 ($\epsilon$=2,300), 340 nm ($\epsilon$=2,700).

C.

16β-Methyl-1,3,5(10),6,8,14-19-Nor-Pregnahexaene-3,11β,17α,21-Tetrol-20-One 21-Acetate To a solution of 16β-methyl-1,3,5(10),6,8-19-nor-pregnapentaene-3,11β,17α,21-tetrol-20-one 21-acetate (199 mg.) in dioxane (5 ml.) add DDQ (170 mg.) and stir at room temperature for 30 minutes. Chromatograph the reaction mixture directly on silica gel GF preparative plates using a chloroform:ethyl acetate (1:1) solvent system. Extract the major band with ethyl acetate, evaporate the combined extracts, and crystallize the resultant residue from ethyl acetate to obtain 16β-methyl-1,3,5(10),6,8,14-19-nor-pregnahexaene-3,11β,17α,21-tetrol-20-one 21-acetate; yield 91 mg.; m.p. 185°–195° C.; $\lambda_{max}^{methanol}$ 244 ($\epsilon$=35,100), 254 ($\epsilon$=44,000), 263 ($\epsilon$=44,000), 285 sh ($\epsilon$=12,400), 295 ($\epsilon$=16,000), 306 ($\epsilon$=14,900), 337 ($\epsilon$=2,600), 354 nm ($\epsilon$=2,200).

EXAMPLE 15

16β-METHYL-1,3,5(10),6,8,14-19-NOR-PREGNAHEXAENE-3,17α,21-TRIOL-11,20-DIONE 21-ACETATE

A.

16β-Methyl-1,4,6,8-Pregnatetraene-17α,21-Diol-3,11,20-Trione 21-Acetate

To a solution of 16β-methyl-1,4,6,8-pregnatetraene-11β,17α,21-triol-3,20-dione 21-acetate (500 mg.) in methylene chloride (50 ml.) add finely powdered manganese dioxide (5 gms.), and stir at room temperature for 20 hours. Separate the manganese dioxide by filtration and wash with methylene chloride. Evaporate the combined filtrate and methylene chloride washings and crystallize the resultant residue from ether to yield 16β-methyl-1,4,6,8-pregnatetraene-17α,21-diol-3,11,20-trione 21-acetate; m.p. 185°–188° C. $\lambda_{max}^{methanol}$ 215 ($\epsilon$=19,400); 273 ($\epsilon$=13,600); 382 nm $\epsilon$=7,300), $[\alpha]_D^{26}$+1164° (CHCl$_3$).

B.
16β-Methyl-1,3,5(10),6,8-19-Nor-Pregnapentaene-3,17α,21-Triol-11,20-Dione 21-Acetate To a solution of 16β-methyl-1,4,6,8-pregnatetraene-17α,21-diol-3,11,20-trione 21-acetate (200 mg.) in tetrahydrofuran (50 ml.) add 1 N hydrochloric acid (5 ml.) and stir the reaction mixture for 1 hour. Pour into 500 ml. saturated aqueous sodium chloride and extract with ethyl acetate. Wash the combined extracts with saturated sodium chloride and evaporate to a volume of about 10 ml. Separate the resultant crystalline precipitate by filtration and dry to obtain 16β-methyl-1,3,5(10),6,8-19-nor-pregnapentaene-3,17α,21-triol-11,20-dione 21-acetate.

C.
16β-Methyl-1,3,5(10),6,8,14-19-Nor-Pregnahexaene-3,17α,21-Triol-11,20-Dione 21-Acetate In a manner similar to that described in Example 14C, treat 16β-methyl-1,3,5(10),6,8-19-nor-pregnapentaene-3,17α,21-triol-11,20-dione 21-acetate with DDQ in dioxane and isolate the resultant product in a manner similar to that described to obtain 16β-methyl-1,3,5(10),6,8,14-19-nor-pregnahexaene-3,17α,21-triol-11,20-dione 21-acetate.

EXAMPLE 16
16α-METHYL-1,3,5(10),6,8,14-19-NOR-PREGNAHEXAENE-3,11β,17α,21-TETROL-20-ONE

A.
16α-Methyl-17α,20;20,21-Bismethylenedioxy-1,3,5(10),6,8,14-19-Nor-Pregnahexaene-3-ol-11-One To a solution of 16α-methyl-1,3,5(10),6,8,14-19-nor-pregnahexaene-3,17α,21-triol-11,20-dione (4.3 gms.) in methylene chloride (200 ml.) under an atmosphere of nitrogen add formaldehyde (200 ml., 37% aqueous solution) and concentrated hydrochloric acid (200 ml.). Stir the mixture at room temperature for 4 hours, separate the two layers, extract the aqueous layer with methylene chloride, combine the organic layer and the methylene chloride extracts and wash with aqueous sodium bicarbonate, then with water. Evaporate the organic solution and chromatograph the resultant residue over silica gel eluting with a petroleum ether/ether gradient. Combine the like fractions containing the desired product as determined by thin layer chromatography and evaporate and crystallize the resultant residue from ether to obtain 16α-methyl-17α,20;20,21-bismethylenedioxy-1,3,5(10),6,8,15-19-nor-pregnahexaene-3-ol-11-one.

B.
16α-Methyl-17α,20;20,21-Bismethylenedioxy-1,3,5(10),6,8,14-19-Nor-Pregnahexaene-3,11β-Diol To a solution of 16α-methyl-17α,20;20,21-bismethylene-dioxy-1,3,5(10),6,8,14-19-nor-pregnahexaene-3-ol-11-one (2 gms.) in tetrahydrofuran:methanol (100 ml., 1:1) dried over alumina at 0° C., add sodium borohydride (3 equivalents, 575 mg.) in portions over a 5-minute period. Stir the reaction mixture for an additional 15 minutes, then add glacial acetic acid dropwise until the solution is neutral. Pour the reaction mixture into water, extract with ethyl acetate, wash the combined extracts with water and evaporate. Chromatograph the resultant residue over silica gel eluting with chloroform:ethyl acetate gradient. Combine the like eluates as determined by thin layer chromatography to obtain 16α-methyl-17α,20;20,21-bismethylenedioxy-1,3,5(10),6,8,14-19-nor-pregnahexanene-3,11α-diol (from the combined early fractions) and 16α-methyl-17α,20;20,21-bismethylenedioxy-1,3,5(10),6,8,14-19-nor-pregnahexaene-3,11β-diol (from the combined like later fractions). Purify by crystallization from ether.

C.
16α-Methyl-1,3,5(10),6,8,14-Nor-Pregnahexaene-3,11β,17α,21-Tetrol 20-One Add a suspension of 16α-methyl-17α,20,20,21-bismethylene-dioxy-1,3,5(10),6,8,14-19-nor-pregnahexaene-3,11β-diol (990 mg., 2.5 mmol) to aqueous 45% hydrofluoric acid (2.5 ml.) at 0° C. and stir the resulting suspension at 0° C. for 1.5 hours. Bring the reaction mixture to neutrality by adding aqueous 5% potassium bicarbonate, then extract with ethyl acetate, wash the combined extracts with water and evaporate to a small volume. Separate the resultant crystals by filtration and dry to obtain 16α-methyl-1,3,5(10),6,8,14-19-nor-pregnahexaene-3,11β,17α,21-tetrol 20-one.

EXAMPLE 17
ALTERNATE PREPARATION OF 16α-METHYL-1,3,5(10),6,8,14-19-NOR-PREGNAHEXAENE-3,17α,21-TRIOL-20-ONE 21-ACETATE

To a solution of 9α,11β-dichloro-16α-methyl-1,4-pregnadiene-17α,21-diol-3,20-dione 21-acetate (31 gms.) in dioxane (1.8 liters) add a solution of hydrogen chloride gas (66 gms.) in dioxane (420 ml.) and DDQ (18.75 gms.). Stir the reaction mixture on a steam bath for 48 hours, then at room temperature for 40 hours. Concentrate the reaction mixture in vacuo to a low volume, then chromatograph the resultant residue over alumina (activity V) eluting with ether. Evaporate the combined eluates and recrystallize the resultant residue from acetone:hexane to obtain 16α-methyl-1,3,5(10),6,8,14-19-nor-pregnahexaene-3,17α,21-triol-20-one 21-acetate.

EXAMPLE 18
16α-METHYL-1,3,5(10),6,8,14-19-NOR-PREGNAHEXAENE-3,11β,17α,21-TETROL-20-ONE

To a solution of 16α-methyl-1,3,5(10),6,8,14-19-nor-pregnahexaene-3,11β,17α,21-tetrol-20-one 3,17α,21-tripropionate (271 mg.) in methanol (25 ml.) add sodium bicarbonate (3.0 ml., 5% aqueous solution) and stir overnight at room temperature. Add dilute hydrochloric acid until the reaction mixture is at about pH 7, then remove the methanol in vacuo. Add water to the resultant residue and extract with ether. Wash the combined ether extracts with water, dry over magnesium sulfate and evaporate. Crystallize the resultant residue from methylene chloride/ether to obtain 16α-methyl-1,3,5(10),6,8,14-19-nor-pregnahexaene-3,11β,17α,21-tetrol-20-one, yield 44 mg.; m.p,. 160°–163° C.; $[\alpha]_D^{26} -161°$ (dioxane), $\lambda_{max}^{methanol}$ 263 sh ($\epsilon=24,600$); 245 ($\epsilon=31,000$); 255 ($\epsilon=38,000$); 264 ($\epsilon=38,700$); 286 sh ($\epsilon=12,800$); 296 ($\epsilon=16,200$); 308 ($\epsilon=15,100$); 338 nm ($\epsilon=2,700$).

We claim:
1. The method of eliciting a mitotic inhibitory response in a warm-blooded animal having a disease characterized by rapid cell proliferation which comprises administering to said animal a non-toxic, mitotic inhibi- tory effective amount of a 19-nor-pregnahexaene-20-one of the following formula I:

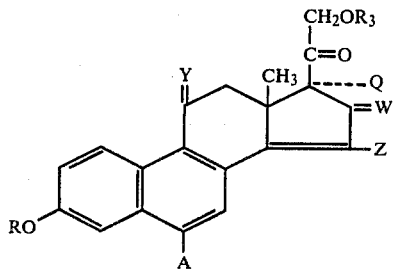

wherein
- A is hydrogen, lower alkyl, fluoro, fluoromethyl, difluoromethyl, or trifluoromethyl;
- R is hydrogen, lower alkyl, or an acyl radical of a hydrocarboncarboxylic acid having up to 20 carbon atoms;
- Y is (H,H), (H,OH), or oxygen;
- W is (H,H); (H, lower alkyl); (Hα hydroxy); (H-α OR$_1$), wherein R$_1$ is an acyl radical of a hydrocarboncarboxylic acid having up to 20 carbon atoms; or =CHT wherein T is hydrogen, lower alkyl, fluorine, or chlorine;
- Q is OR$_2$ wherein R$_2$ is hydrogen or an acyl radical of a hydrocarboncarboxylic acid having up to 20 carbon atoms; hydrogen provided W is (H,H), or (H, lower alkyl); or Q and W together is a 16α,17α-lower alkylidenedioxy;
- Z is hydrogen, chlorine or bromine;
- R$_3$ is hydrogen or an acyl radical of a hydrocarbon-carboxylic acid having up to 20 carbon atoms; or OR$_3$ together with Q is a member selected from the group consisting of alkylidenedioxy and alkylorthoalkanoate;
- and when Q is hydroxy and R$_3$ is hydrogen, the 17α,20;20,21-bismethylenedioxy derivatives thereof;
- together with a non-toxic pharmaceutically acceptable carrier.

2. The method of claim 1 wherein said disease is a skin disease characterized by rapid cell proliferation.

3. The method of claim 2 when said 19-nor-pregnahexaene-20-one is administered topically, which is the method of reducing epidermal mitosis in a warm-blooded animal having a skin disease characterized by rapid cell proliferation which comprises applying topically to the affected area in a concentration effective for reducing epidermal mitosis, a 19-nor-pregnahexaene-20-one of formula I in claim 1, together with a non-toxic, pharmaceutically acceptable carrier.

4. The method of claim 3 wherein said skin disease is psoriasis, which is the method of treating and controlling psoriasis which comprises applying topically to the affected area in a concentration effective for the treatment of psoriasis, a 19-nor-pregnahexaene-20-one of formula I in claim 1, together with a non-toxic, pharmaceutically acceptable carrier.

5. The method of claim 4 when carried out with a 1,3,5(10), 6,8,14-19-nor-pregnahexaene-20-one of formula I wherein W is (H, lower alkyl).

6. The method of claim 5 when carried out with a compound of structural formula II:

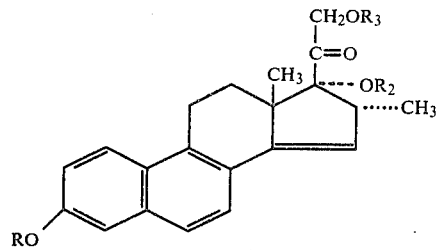

wherein
- R is hydrogen, lower alkyl, or an acyl radical of a hydrocarboncarboxylic acid having up to 8 carbon atoms;
- R$_2$ and R$_3$ are each hydrogen or an acyl radical of a hydrocarboncarboxylic acid having up to 8 carbon atoms.

7. The method of claim 6 when carried out with a 1,3,5(10), 6,8,14-19-nor-pregnahexaene-20-one of formula II wherein R$_2$ is hydrogen, R$_3$ is acetyl, and R is hydrogen, acetyl or benzoyl.

8. The method of claim 6 when carried out with 16α-methyl-1,3,5(10),6,8,14-19-nor-pregnahexaene-3,17α,21-triol-20-one 21-acetate.

9. A pharmaceutical composition for the treatment of psoriasis comprising an anti-psoriatically effective amount of a 19-nor-pregnahexaene-20-one of formula I in claim 1, together with a non-toxic pharmaceutically acceptable carrier.

10. The composition of claim 9 which is a composition for topical administration.

11. A topical pharmaceutical composition of claim 10 wherein said 19-nor-pregnahexaene-20-one is a 19-nor-pregnahexaene-20-one of formula II in claim 6.

12. A composition of claim 11 wherein said 19-nor-pregnahexaene-20-one of formula II in claim 6 is 16α-methyl-1,3,5(10), 6,8,14-19-nor-pregnahexaene-3,17α,21-triol-20-one, or the 21-acetate, 3,21-diacetate or 3-benzoate 21-acetate thereof.

13. The composition of claim 11 comprising an anti-psoriatically effective amount of 16α-methyl-1,3,5(10),6,8,14-19-nor-pregnahexaene-3,17α,21-triol-20-one 21-acetate together with a non-toxic, pharmaceutically acceptable carrier.

14. A 19-nor-pregnahexaene-20-one of the following formula:

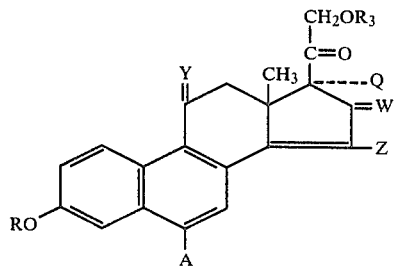

wherein
- A is hydrogen, lower alkyl, fluoro, fluoromethyl, difluoromethyl, or trifluoromethyl;
- R is hydrogen, lower alkyl, or an acyl radical of a hydrocarboncarboxylic acid having up to 20 carbon atoms;
- Y is (H,H), (H,OH) or oxygen;

W is (H,H) provided at least one of Y and Z is other than hydrogen; (H, lower alkyl); (H-α hydroxy); (H-α OR$_1$), wherein R$_1$ is an acyl radical of a hydrocarboncarboxylic acid having up to 20 carbon atoms; or =CHT wherein T is hydrogen, lower alkyl, fluorine, or chlorine;

Q is OR$_2$ wherein R$_2$ is hydrogen or an acyl radical of a hydrocarboncarboxylic acid having up to 20 carbon atoms; hydrogen provided W is (H,H), or (H, lower alkyl); or Q and W together is a 16α,17α-lower alkylidenedioxy;

Z is hydrogen, chlorine or bromine;

R$_3$ is hydrogen or an acyl radical of a hydrocarboncarboxylic acid having up to 20 carbon atoms; or OR$_3$ together with Q is a member selected from the group consisting of alkylidenedioxy and alkylorthoalkanoate;

and when Q is hydroxy and R$_3$ is hydrogen, the 17α,20;20,21-bismethylenedioxy derivatives thereof.

15. A compound of claim 14 wherein W is (H, lower alkyl).

16. A compound of claim 14 wherein Y is (H,H), W is (H, lower alkyl), and Z is hydrogen.

17. A compound of claim 16 of structural formula II:

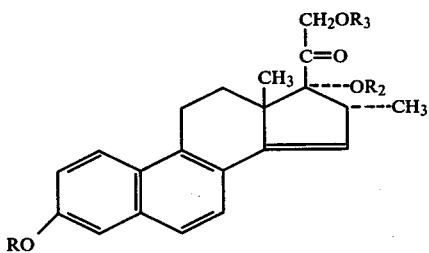

wherein

R is hydrogen, lower alkyl, or an acyl radical of a hydrocarboncarboxylic acid having up to 8 carbon atoms;

R$_2$ and R$_3$ are each hydrogen or an acyl radical of a hydrocarboncarboxylic acid having up to 8 carbon atoms.

18. A compound of claim 17 wherein R$_2$ is hydrogen, R$_3$ is acetyl, and R is hydrogen, acetyl or benzoyl.

19. A compound of claim 18 which is 16α-methyl-1,3,5(10),6,8,14-19-nor-pregnahexaene-20-one 21-acetate.

20. A compound of claim 14 which is 15-chloro-16α-methyl-1,3,5(10),6,8,14-19-nor-pregnahexaene-3,17α,21-triol-20-one 21-acetate.

21. The process for the preparation of a 15-halogeno-1,3,5(10),6,8,14-19-nor-pregnahexaene-3,17α,21-triol-20-one of claim 14 which comprises the reaction of the corresponding 15-unsubstituted-1,3,5(10),6,8-19-nor-pregnapentaene-3,17α,21-triol-20-one, in which any 21-hydroxyl group present is protected, in an aprotic solvent with at least two molar equivalents of 2,3-dichloro-5,6-dicyanobenzoquinone in the presence of at least a molar equivalent of hydrogen halide, said halide being chloride or bromide.

22. The process of claim 17 wherein any 21-hydroxyl group is protected by a lower alkanoate ester, said aprotic solvent is dioxane, and said hydrogen halide is hydrogen chloride.

23. The process for the preparation of 15-chloro-16α-methyl-1,3,5(10),6,8,14-19-nor-pregnahexaene-3,17α,21-triol-20-one 21-acetate, which comprises the reaction of 16α-methyl-1,3,5(10),6,8-19-nor-pregnapentaene-3,17α,21-triol-20-one 21-acetate in dioxane with at least two molar equivalents of 2,3-dichloro-5,6-dicyanobenzoquinone and with at least a molar equivalent of hydrogen chloride.

* * * * *